(12) United States Patent
Weitzman et al.

(10) Patent No.: US 12,721,636 B2
(45) Date of Patent: Sep. 1, 2026

(54) DEVICE SYSTEM AND METHOD FOR ROBOTIC SPINAL DECOMPRESSION

(71) Applicant: CAREVATURE MEDICAL LTD., Rehovot (IL)

(72) Inventors: Yoseph Weitzman, Tel Aviv (IL); Eran Miller, Moshav Beit Elazari (IL)

(73) Assignee: CAREVATURE MEDICAL LTD., Rehovot (IL)

( * ) Notice: Subject to any disclaimer, the term of this patent is extended or adjusted under 35 U.S.C. 154(b) by 360 days.

(21) Appl. No.: 18/130,349

(22) Filed: Apr. 3, 2023

(65) Prior Publication Data

US 2023/0240692 A1 Aug. 3, 2023

Related U.S. Application Data

(63) Continuation of application No. PCT/IL2021/051195, filed on Oct. 5, 2021.

(60) Provisional application No. 63/088,135, filed on Oct. 6, 2020.

(51) Int. Cl.

| | |
|---|---|
| ***A61B 17/16*** | (2006.01) |
| ***A61B 17/32*** | (2006.01) |
| *A61B 90/20* | (2016.01) |

(52) U.S. Cl.
CPC .... *A61B 17/1671* (2013.01); *A61B 17/32002* (2013.01); *A61B 90/20* (2016.02)

(58) Field of Classification Search
CPC ................ A61B 17/02; A61B 17/1671; A61B 17/32002; A61B 2017/00318; A61B 2017/00327; A61B 2017/00991; A61B 2017/320032; A61B 2017/3443; A61B 2034/105; A61B 2034/2048; A61B 2034/2055; A61B 2090/064; A61B 2090/08021; A61B 2090/371; A61B 2218/002; A61B 2218/007; A61B 34/30; A61B 90/20
See application file for complete search history.

(56) References Cited

U.S. PATENT DOCUMENTS

| | | | | |
|---|---|---|---|---|
| 2010/0249800 | A1 | 9/2010 | Kim et al. | |
| 2012/0303125 | A1* | 11/2012 | Gharib | A61N 1/36142 623/17.16 |
| 2014/0330434 | A1* | 11/2014 | Nixon | A61B 34/70 700/254 |
| 2016/0279388 | A1* | 9/2016 | Barrish | A61M 25/1036 |
| 2019/0374236 | A1* | 12/2019 | Weitzman | A61B 17/32002 |

OTHER PUBLICATIONS

PCT International Search Report for International Application No. PCT/IL2021/051195, mailed Jan. 18, 2022, 3pp.
PCT Written Opinion for International Application No. PCT/IL2021/051195, mailed Jan. 18, 2022, 15pp.
PCT International Preliminary Report on Patentability for International Application No. PCT/IL2021/051195, issued Mar. 28, 2023, 16pp.

* cited by examiner

*Primary Examiner* — Scott Luan
(74) *Attorney, Agent, or Firm* — The Roy Gross Law Firm, LLC; Roy D. Gross

(57) ABSTRACT

Disclosed are robotic systems, surgical instruments for used therewith as well as methods of utilizing same in spinal decompression surgeries.

18 Claims, 23 Drawing Sheets
(4 of 23 Drawing Sheet(s) Filed in Color)

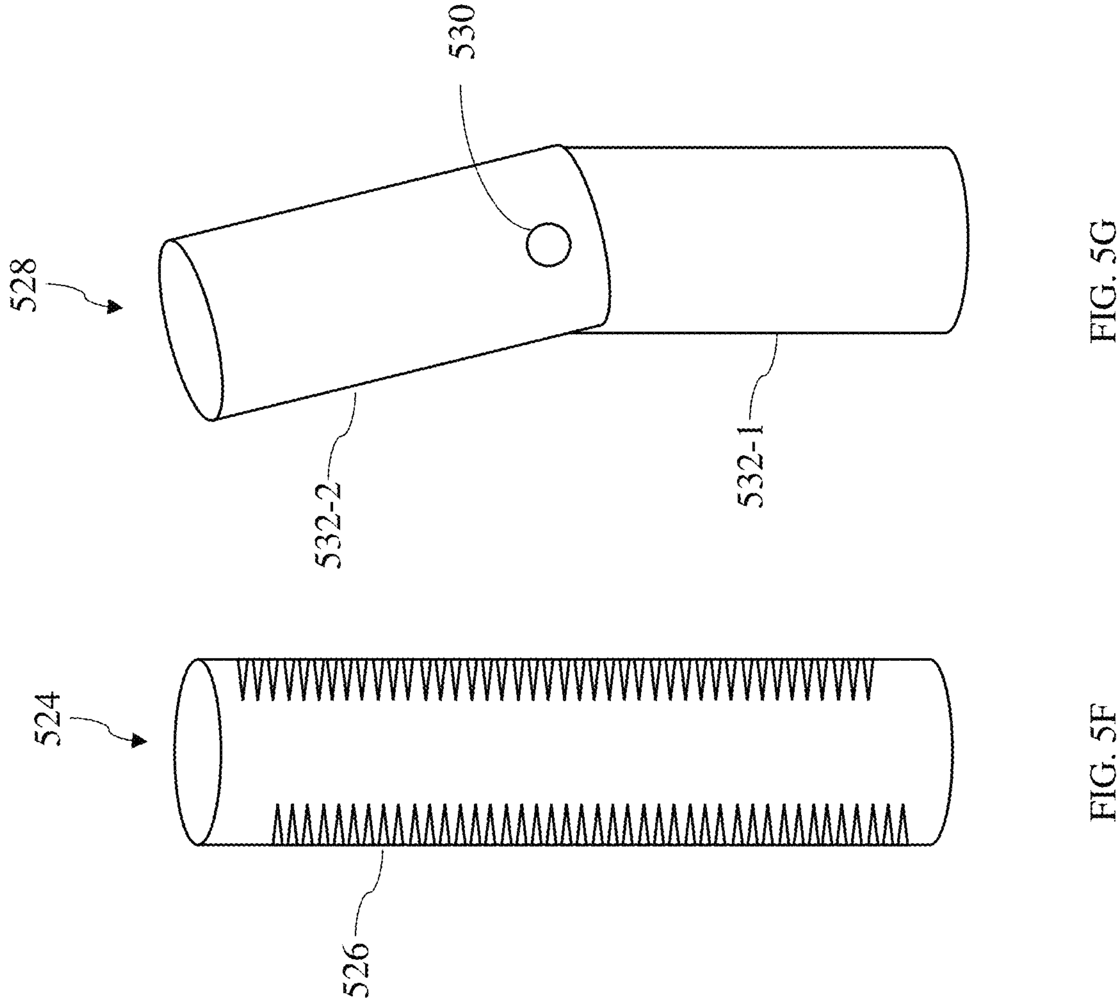
FIG. 5G
FIG. 5F
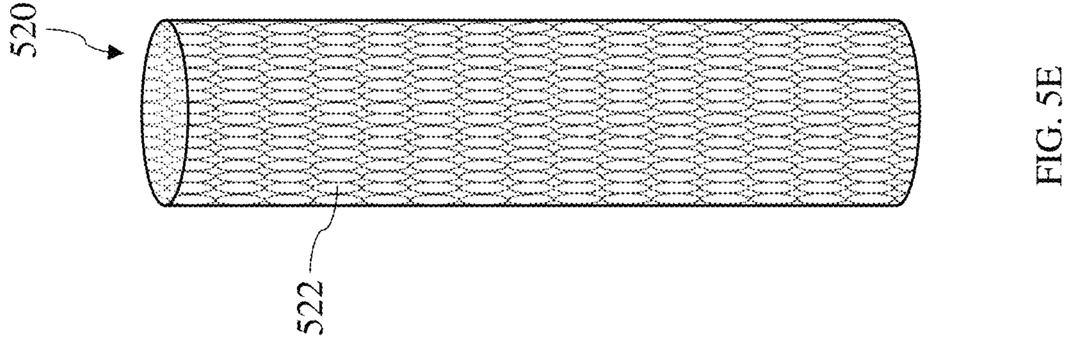
FIG. 5E 1000
1004
1006
1008
1010
1012
1002

900
904
902
906

908
L
900
904
902

1018
1004
1002
1016

1018
1004
1002
β
E
D

DEVICE SYSTEM AND METHOD FOR ROBOTIC SPINAL DECOMPRESSION

CROSS REFERENCE TO RELATED APPLICATIONS

This application is a Bypass Continuation of PCT Patent Application No. PCT/IL2021/051195 having International filing date of Oct. 5, 2021, which claims the benefit of priority of U.S. Provisional Patent Application No. 63/088,135, filed Oct. 6, 2020, the contents of which are all incorporated herein by reference in their entirety.

TECHNICAL FIELD OF THE INVENTION

The present disclosure generally relates to devices and methods for removing tissue from a body, and more particularly, but not exclusively, to methods and devices for minimally invasive removal of tissue from anatomically constrained sites without damaging surrounding non-targeted tissues, such as nerves.

BACKGROUND OF THE INVENTION

Excess body tissue can lead to pathological conditions giving rise to pain, especially when the excess body tissue impinges on a nerve. One such common condition is spinal stenosis: narrowing (stenosis) of the spinal canal, due to excess bone tissue pressing on the spinal cord and resulting in a neurological deficit. Other such common conditions include bulging or herniated discs, which are associated with osteophyte formation in the spinal canal.

Standard treatments for spinal stenosis include corpectomy, laminectomy, and osteotomy: surgical procedures involving removing from a vertebra any bone spurs pressing on the spinal cord, and thereby decompressing the spinal cord and nerves and alleviating the neurological deficit.

These surgical procedures, and others, require selective removal of target tissue—which is often difficult to reach—while avoiding damage to surrounding tissue. This task is made doubly difficult when, in addition, the target tissue is hard tissue, such as resulting from excess bone growth on a vertebra.

SUMMARY OF THE INVENTION

The present disclosure relates to robotic systems for performing spinal decompression surgery comprising: a robot arm having multi-degree of freedom; and a surgical instrument configured to be received by the robotic arm.

According to some embodiments, the robotic arm is a "master-slave"-type robotic arm, i.e. a robotic arm directly controlled by a human operator. According to some embodiments, the robotic arm is a remote-controlled robotic arm, i.e. a robotic arm controlled.

According to some embodiments, the surgical instrument comprises an elongated hollow tubular member comprising a first bend at a distal end thereof, a flexible drive shaft positionable within the elongated hollow tubular member, and an end effector, wherein the drive shaft is configured to transfer torque and rotational or reciprocal speed of at least 10,000 rpm, from a proximal end of the elongated member, through the bend and to the end effector. According to some embodiments, the angle of the bend is adjustable. According to some embodiments, the surgical instrument comprises a shield configured to cover a portion of the end effector. According to some embodiments, the position of the shield in relation to the end effector is adjustable.

According to some embodiments, the robotic system includes a processor configured to control and/or provide instructions regarding the position of the robot arm and/or the surgical instrument. According to some embodiments, the robotic system includes a driving unit configured to control the operation of the surgical instrument, based on inputs from the processor. According to some embodiments, the robotic system includes a user operated control unit configured to provide control operations to the processor.

According to some embodiments, the processor is configured to control the angle of the bend.

According to some embodiments, the end effector includes a cutting head. According to some embodiments, the end effector includes a camera or an optical array. According to some embodiments, the end effector includes a suction tip.

Advantageously, the herein disclosed robotic system enables controlling the operation (orientation, position etc) of the surgical instrument with multiple degrees of freedom, such as 2 degrees of freedom, 3 degrees of freedom, 4 degrees of freedom, 5 degrees of freedom, 6 degrees of freedom, 7 degrees of freedom or more. Each possibility is a separate embodiment.

As a further advantage, the robotic arm enables maintaining the surgical instrument at a fixed position for a prolonged period of time, thereby increasing the safety of the procedure, e.g. due to a minimized risk of damaging nerves within or proximal to the surgical site.

According to some embodiments, the flexible drive shaft comprises a core made of a plurality of stranded or braided wires and at least one outer layer, the outer layer made of wires wound around the core.

According to some embodiments, the surgical instrument includes a sensor positioned at the elongated shaft, the sensor configured to provide feedback to the processor regarding operation of the surgical instrument. According to some embodiments, the sensor is a force sensor configured to provide a signal indicative of a tactile feedback response.

According to some embodiments, the surgical instrument includes a suction channel configured for suction of debris.

According to some embodiments, the end effector is elongatable along its longitudinal axis.

This may advantageously enable advancement of end effector vis-à-vis the tissue, while maintaining the robotic arm and/or the surgical instrument in a fixed position.

According to some embodiments, one or more sections of the elongated hollow tubular member is elongatable. This may advantageously enable advancement of surgical instrument vis-à-vis the tissue, while maintaining the robotic arm and/or the surgical instrument in a fixed position.

According to some embodiments, the surgical instrument comprises a proximal torque transfer element positioned within the elongated hollow tubular member, the proximal torque transfer element connected to a proximal end of the flexible drive shaft. According to some embodiments, the surgical instrument comprises a distal torque transfer element connected to a distal end of the flexible drive shaft. According to some embodiments, the proximal and/or distal torque transfer element is elongatable. This may advantageously enable advancement of end effector vis-à-vis the tissue, while maintaining the robotic arm and/or the surgical instrument in a fixed position.

According to some embodiments, the processor is configured to control and/or provide instruction to the surgical instrument regarding the elongation of one or more of the end effector, the elongated hollow tubular member, the proximal torque transfer element and the distal torque transfer element. Each possibility is a separate embodiment.

According to some embodiments, the elongated hollow tubular member includes a shield configured to cover a portion of the end effector. According to some embodiments, the elongated hollow tubular member terminates with a shield configured to cover at least a portion of the end effector. According to some embodiments, the shield is rotatable, so as to allow coverage of different portions of the end effector. According to some embodiments, the angle of the shield relative to the end effector is adjustable. According to some embodiments, the shield is extendable. It is understood that such maneuverability of the shield enables changing the orientation of the exposed part of the end effector during operation and without rotating the surgical instrument and/or without changing the position/orientation of the robotic arm.

According to some embodiments, the processor is configured to control the rotation, the angle and/or the extension of the shield.

According to some embodiments, the distal end of the elongated hollow tubular member comprises one or more cameras configured for imaging of and area surrounding the end effector. According to some embodiments, the one or more cameras is 1, 2, 3, 4 or more cameras. According to some embodiments, the one or more cameras are configured to provide circumferential imaging around the end effector. According to some embodiments, the one or more cameras are configured to provide imaging around part of the end effector, which is not covered by the shield. According to some embodiments, the camaras are configured to be circumferentially moved/rotated around the elongated member so as to provide imaging at different circumferential positions of the end effector. According to some embodiments, the processor is configured to control the position of the one or more cameras.

According to some embodiments, the processor is configured to receive images from the one or more cameras. According to some embodiments, the processor is configured to adjust the position of the robot arm and/or of the surgical instrument, based on the images received from the one or more cameras.

According to some embodiments, the surgical instrument comprises a handle. According to some embodiments, the elongated hollow tubular member is axially rotatable relative to the handle. According to some embodiments, the processor is configured to control the orientation of the elongated hollow tubular member. It is understood that such maneuverability of the elongated member relative to the handle enables changing the orientation of the exposed part of the end effector during operation, without rotating the surgical instrument and/or without changing the position/orientation of the robotic arm.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE FIGURES

The patent or application file contains at least one drawing executed in color. Copies of this patent or patent application publication with color drawing(s) will be provided by the Office upon request and payment of the necessary fee.

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show details of an embodiment in more detail than is necessary for a fundamental understanding of the teachings of the disclosure.

FIG. 5A, FIG. 5B, FIG. 5C, FIG. 5D, FIG. 5E, FIG. 5F and FIG. 5G are perspective view schematic illustrations of bending mechanisms, in accordance with some embodiments of the present invention;

DETAILED DESCRIPTION OF THE INVENTION

Figure 1:
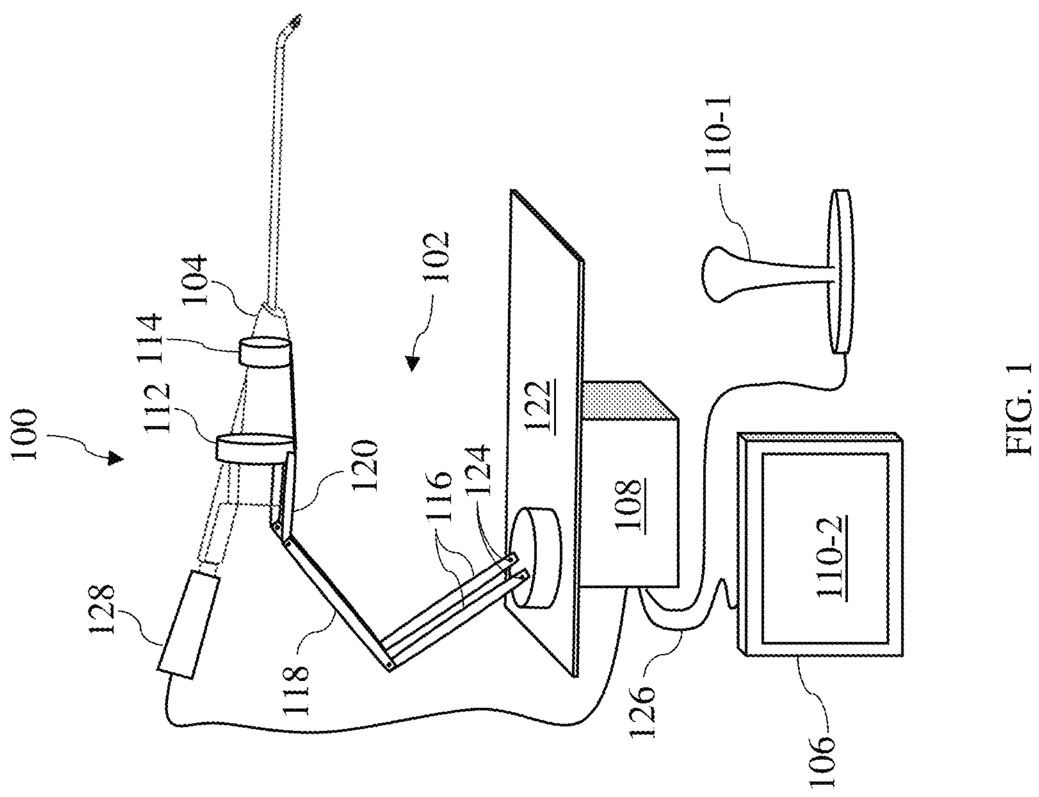
FIG. 1 is a schematic illustration of an exemplary robotic system for spinal decompression surgery, in accordance with some embodiments of the present invention.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided herein a system, a device, and a method for automated spinal decompression. According to some embodiments, the system comprises a robotic arm, a surgical instrument, a processor, and a driving unit, configured to be controlled by a human operator and/or the processor. According to some embodiments, the robotic arm is a "master-slave"-type robotic arm. According to some embodiments, the robotic arm is a remote-controlled robotic arm.

According to some embodiments, the surgical instrument comprises an elongated hollow tubular member comprising a first bend at a distal end thereof, a flexible drive shaft positionable within the elongated hollow tubular member, and an end effector, wherein the drive shaft is configured to transfer torque and rotational speed of at least 10,000 rpm, from a proximal end of the elongated member, through the bend and to the end effector. According to some embodiments, the angle of the bend is adjustable.

According to some embodiments, the robotic system includes a processor configured to control and/or provide instructions regarding the position of the robot arm and/or the surgical instrument. According to some embodiments, the robotic system includes a driving unit configured to control the operation of the surgical instrument, based on inputs from the processor. According to some embodiments, the robotic system includes a user operated control unit configured to provide control operations to the processor.

According to some embodiments, the surgical instrument comprises a handle and an elongated hollow tubular member. According to some embodiments, the handle and the elongated hollow tubular member are removably and/or rotatably coupled. According to some embodiments, the elongated hollow tubular member is axially rotatable relative to the handle.

According to some embodiments, the elongated hollow tubular member comprises one or more elongatable sections. According to some embodiments, one or more section of the elongated hollow tubular member comprises an elongation mechanism configured to change the length of the one or more section of the elongated hollow tubular member comprises an elongation mechanism. According to some embodiments, the processor is configured to control the length of the elongated hollow tubular member.

According to some embodiments, the elongated hollow tubular member comprises one or more bent portions. According to some embodiments, the one or more bent portion are bendable using one or more bending mechanisms. According to some embodiments, the angle of the bend of the one or more bent portions is adjustable. According to some embodiments, the processor is configured to control the angle of the bend.

According to some embodiments, the surgical instrument comprises the flexible drive shaft, wherein the flexible drive shaft comprises a core made of a plurality of stranded or braided wires and at least one outer layer comprising a layer of wires wound around the core. According to some embodiments, one or more portion of the flexible drive shaft comprises an elongation mechanism and is elongatable.

According to some embodiments, the flexible drive shaft is coupled to one or more torque transfer elements configured to transfer torque form the driving unit to the end effector. According to some embodiments, the flexible drive shaft is coupled to a proximal torque transfer element at a proximal end of the flexible drive shaft. According to some embodiments, the flexible drive shaft is coupled to a distal torque transfer element at a distal end of the flexible drive shaft. According to some embodiments, the one or more torque transfer elements comprise an elongation mechanism and are elongatable along a longitudinal axis thereof.

According to some embodiments, the flexible drive shaft and/or the distal torque transfer element is coupled to the end effector and configured to rotate the end effector at a rotational speed of at least 10,000 rpm. According to some embodiments, the rotation may be continuous rotation. According to some embodiments, the rotation may be reciprocal rotation. According to some embodiments, the end effector may be a cutting head. According to some embodiments, the end effector may be a camera. According to some embodiments, the end effector may be an optical array. According to some embodiments, the end effector may be an endoscope. According to some embodiments, the end effector may be a suction tip. According to some embodiments, the end effector comprises an elongation mechanism. According to some embodiments, the end effector is elongatable along a longitudinal axis thereof.

According to some embodiments, the surgical instrument comprises one of more shields configured to cover one or more portions of the end effector. According to some embodiments, the one or more shields are moveably coupled to elongated hollow tubular member. According to some embodiments, the one or more shields comprise a rotation mechanism and are rotatable within the elongated hollow tubular member and/or about a longitudinal axis of the elongated hollow tubular member. According to some embodiments, the angle of the shield in relation to the end effector is adjustable. According to some embodiments, the rotation may be continuous rotation. According to some embodiments, the rotation may be reciprocal rotation.

According to some embodiments, the shield comprises an extension mechanism and is extendable in relation to the elongated hollow tubular member. According to some embodiments, the shield comprises an elongation mechanism and are elongatable along a plurality of directions in relation to the end effector and/or the elongated hollow tubular member. According to some embodiments, the shield is coupled to the drive unit and/or to the processor such that the processor is configured to control the rotation, the angle and/or the length of the shield.

According to some embodiments, the surgical instrument comprises a suction channel configured for suction of debris. According to some embodiments, the suction channel extends along the elongated hollow tubular member. According to some embodiments, the suction channel extends between the end effector and an inner surface of a wall of the elongated hollow tubular member. According to some embodiments, the suction channel is positioned within the wall of the elongated hollow tubular member.

According to some embodiments, the suction channel is coupled to a suction unit configured for suction of debris. According to some embodiments, the suction unit is coupled to the drive unit and/or to the processor such that the processor commands the operation of the suction unit. According to some embodiments, the system and/or the surgical instrument comprises one or more sensors. According to some embodiments, the one or more sensors are positioned along a length of the elongated hollow tubular member.

According to some embodiments, the one or more sensors are in communication with the processor. According to some embodiments, the processor is configured to receive data from the one or more sensors. According to some embodiments, the at least one sensor comprises one or more of a force sensor, a pressure sensor, temperature sensor, speedometer, accelerometer, proximity sensor, and infra-red sensor, or any combination thereof.

According to some embodiments, the processor is configured to control the elongation of one or more of the end effector, the elongated hollow tubular member, the proximal torque transfer element and the distal torque transfer element, based on data received from the one or more sensors. According to some embodiments, the processor is configured to control the spatial orientation of one or more of the end effector and the shield based on data received from the one or more sensors.

According to some embodiments, the system and/or the surgical instrument comprises one or more cameras configured for imaging of and area surrounding the end effector. According to some embodiments, the one or more cameras are coupled to the elongated hollow tubular member. According to some embodiments, the processor is configured to receive images from the one or more cameras. According to some embodiments, the processor is configured to adjust positioning of the robot arm and or of the surgical instrument based on the images received from the one or more cameras.

According to some embodiments of the present invention, the surgical instrument is standalone, and thereby does not require additional systems in order to operate. According to some embodiments, the surgical instrument is couplable with a system, for example, a system comprising a robot arm and/or a driving unit. According to some embodiments, the surgical instrument is couplable to a universal remote. According to some embodiments, the surgical instrument is couplable to a universal system.

According to some embodiments, the system and/or the surgical instrument comprise one or more markers positioned thereon such that an external visualization instrument such as a camera and/or sensor can track the position of the surgical instrument in real time. According to some embodiments, the markers comprise passive markers and/or active markers. According to some embodiments, the position of the one or more markers in relation to the surgical instrument and/or system is stationary and/or is adjustable. According to some embodiments, the system comprises a visualization instrument, wherein the visualization instrument is coupled to the processor. According to some embodiments, and as described in greater elsewhere herein, there is provided a method comprising tracking a position of the surgical instrument in real time in relation to the target tissue. According to some embodiments, the method comprises tracking a position of the surgical instrument by tracking one or more markers in real time. According to some embodiments, the method comprises determining a position of the end effector in relation to the target tissue by calculating a position of the surgical instrument using the location of the detected markers. According to some embodiments, there is provided a method for performing a robotic spinal decompression surgery. According to some embodiments, the method comprises attaching the surgical instrument to a robotic arm. According to some embodiments, the method comprises identifying a location of the target anatomy based on preoperative imaging. According to some embodiments, the method comprises determining an initial orientation of the elongated hollow tubular member based on the preoperative imaging. According to some embodiments, the method comprises determining an initial angle of the bend based on the preoperative imaging.

According to some embodiments, the method comprises determining an initial degree of elongation of one or more of the shield, the end effector, the elongated hollow tubular member, the proximal torque transfer element and the distal torque transfer element based on preoperative imaging.

According to some embodiments, the method comprises advancing the surgical instrument to the target anatomy until engaging bone to be removed. According to some embodiments, the method comprises creating a surgical corridor to the target anatomy based on the preoperative imaging. According to some embodiments, the method comprises exposing the neural element to be decompressed prior to the activating the surgical instrument. According to some embodiments, the method comprises activating rotation of the end effector to a at least 10,000 rpm; thereby causing bone removal. According to some embodiments, the method comprises adjusting an orientation of the elongated hollow tubular member based on images obtained from the one or more cameras during surgery.

According to some embodiments, the method comprises adjusting the angle of the bend based on images obtained from the one or more cameras during surgery. According to some embodiments, the method comprises adjusting the elongation of one or more of the shield the end effector, the elongated hollow tubular member, the proximal torque transfer element and the distal torque transfer element based on preoperative based on images obtained from the one or more cameras during surgery.

Robotic System for Spinal Decompression Surgery

Reference is made to FIG. 1, which is a schematic illustration of an exemplary robotic system for spinal decompression surgery, in accordance with some embodiments of the present invention. According to some embodiments, the system 100 comprises a robot arm 102 having multi-degree of freedom. According to some embodiments, the system 100 comprises a surgical instrument 104 configured to be received by the robotic arm 102. According to some embodiments, the system 100 comprises a processor 106 configured to control the position of the robot arm 102 and/or the surgical instrument 104. According to some embodiments, the system 100 comprises a driving unit 108 configured to control the operation of the surgical instrument 104 based on inputs from the processor 106.

According to some embodiments, and as described in greater detail elsewhere herein, the surgical instrument 104 comprises an elongated hollow tubular member comprising a first bend at a distal end thereof. According to some embodiments, the surgical instrument 104 comprises a flexible drive shaft positionable within the elongated hollow tubular member. According to some embodiments, the surgical instrument 104 comprises an end effector. According to some embodiments, the end effector may include a cutting head. According to some embodiments, the end effector may include a camera. According to some embodiments, the end effector may include a suction tip. According to some embodiments, the drive shaft of the surgical instrument 104 is configured to transfer torque and rotational speed of at least 10,000 rounds per minute (rpm), from a proximal end of the elongated member, through the bend and to the end effector. According to some embodiments, the rotation may be continuous rotation. According to some embodiments, the rotation may be reciprocal rotation.

According to some embodiments, the robot arm 102 is configured to couple with the surgical instrument 104. According to some embodiments, the robot arm 102 and the surgical instrument 104 are removably couplable and comprise a locked state in which a portion of the robot arm 102 and a portion of the surgical instrument 104 are fixed in relation to reach other. According to some embodiments, the robot arm 102 comprises one or more holders 112/114 configured to support at least a portion of the surgical instrument 104. According to some embodiments the surgical instrument 104 is configured to fit into the one or more holders 112/114.

According to some embodiments, the robot arm 102 comprises at least two rods 116 coupled to a base 122. According to some embodiments, the rods 116 are coupled to the base 122 via at least one hinge 124. According to some embodiments, the rods 116 are rotatable in relation to the base 122. According to some embodiments, the base 122 is configured to couple to a surgical bed. According to some embodiments, the at least two rods 116 are rotatably coupled to additional rods 118/120. According to some embodiments, the rods 116 and/or the additional rods 118/120 are coupled to the one or more holders 112/114. According to some embodiments, the one or more holders 112/114 are rotatable in relation to the rods 116 and/or the additional rods 118/120.

According to some embodiments, the robot arm 102 comprises at least three degrees of freedom. According to some embodiments, the robot arm 102 comprises at least five degrees of freedom. According to some embodiments, the robot arm 102 comprises nine degrees of freedom.

According to some embodiments, the one or more holder 112/114 are rotatable about a longitudinal axis of one or more of the rods 116 and the additional rods 118/120, or in other words, a longitudinal axis thereof. According to some embodiments, the one or more holder 112/114 are extendable along at least a portion of a longitudinal axis of one or more of the rods 116 and the additional rods 118/120, or in other words, along a longitudinal axis thereof.

According to some embodiments, the orientation, rotation, the type of rotation, extension, contraction and/or bending of one or more of the robot arm 102 and the surgical instrument 104 is controlled and/or commanded by the processor 106. According to some embodiments, the type of rotation may include any one or more of continuous rotation and reciprocal rotation.

According to some embodiments, the processor 106 is coupled to at least one of the robot arm 102, the surgical instrument 104, and the driving unit 108. According to some embodiments, the processor 106 is coupled to at least one of the robot arm 102, the surgical instrument 104, and the driving unit 108 by a wire or wirelessly. For example, according to some embodiments the processor 106 is coupled to one or more of the robot arm 102, the surgical instrument 104, and the driving unit 108 using a cable, Wi-Fi, and/or Bluetooth. According to some embodiments, and as depicted by FIG. 1, the processor 106 is coupled to the driving unit 108 via a cable 126.

According to some embodiments, the processor 106 commands the orientation, rotation, extension, contraction and/or bending of one or more of the robot arm 102, the one or more rods 116, the one or more additional rods 118/120, and the one or more holder 112/114 by commanding operations of the driving unit 108. According to some embodiments, the driving unit 108 comprises a motor. According to some embodiments, the driving unit 108 comprises a plurality of motors. According to some embodiments, the system 100 comprises one or more actuators 128 coupled to one or more of the robot arm 102 and/or the surgical instrument 104. According to some embodiments, the driving unit 108 is coupled to the surgical instrument 104 via the robot arm 106. According to some embodiments, the driving unit 108 is configured to drive the movement of the robot arm 102 and the surgical instrument 104 separately. According to some embodiments, the driving unit 108 is configured to drive the movement of the robot arm 102 and/or the surgical instrument 104 via the one or more actuators 128. In some embodiments, the one or more actuators 128 is coupled to the driving unit 108 by a wire and/or wirelessly.

According to some embodiments, the driving unit 108 is configured to drive movement of one or more portions of the robot arm 102 in a plurality of directions. According to some embodiments, the driving unit 108 is configured to drive the movement of one or more portions of the robot arm 102 in a plurality of degrees of freedom. According to some embodiments, the driving unit 108 is configured to drive one or more of the rotation, extension, contraction and/or bending of one or more portions of the robot arm 102.

According to some embodiments, and as described in greater detail elsewhere herein, the driving unit 108 is coupled to the surgical instrument 104. According to some embodiments, the driving unit 108 is configured to drive movement of at least a portion of the surgical instrument 104 in a plurality of directions. According to some embodiments, the driving unit 108 is configured to drive the movement of at least a portion of the surgical instrument 104 in a plurality of degrees of freedom. According to some embodiments, the driving unit 108 is configured to control an orientation of the surgical instrument 104 by command of the processor 106. According to some embodiments, and as described in greater detail elsewhere herein, the driving unit 108 is configured to drive one or more of the orientation, rotation, extension, contraction and/or bending of one or more portions of the surgical instrument 104.

According to some embodiments, the system 100 comprises a control unit 110-1/110-2 (refereed to hereinafter as control unit 110) that is configured to provide operative control to the processor 106 by a user. According to some embodiments, the control unit 110 comprises a user interface module. According to some embodiments, the control unit 110 comprises a display screen, e.g., control unit 110-2, and/or at least one button. According to some embodiments, the control unit 110 comprises a remote-control module, such as, for example, a mouse or a joystick, e.g., control unit 110-1. According to some embodiments, the control unit 110 is coupled to and/or in communication with the processor 106. According to some embodiments, the control unit 110 enables a user to command the orientation, rotation, extension, contraction and/or bending of one or more of the robot arm 102 and the surgical instrument 104 by communicating one or more commands to the robot arm 102 and/or the surgical instrument 104 via the processor 106.

According to some embodiments, the system 100 comprises at least one sensor, camera, microscope, and/or endoscope. According to some embodiments, and as described in greater detail elsewhere herein, the sensor, camera, microscope, and/or endoscope are coupled to the surgical instrument 104 and/or the robotic arm 102. According to some embodiments, the sensor, camera, microscope, and/or endoscope are in communication with the processor 106. According to some embodiments, the sensor, camera, microscope, and/or endoscope are configured to provide feedback to the processor 106 regarding operation of the surgical instrument 104. According to some embodiments, the sensor, camera, microscope, and/or endoscope are configured to provide feedback to the processor 106 regarding operation of the robotic arm 102.

According to some embodiments, the sensor comprises a force sensor. According to some embodiments, the at least one sensor comprises one or more of pressure sensor, temperature sensor, speedometer, accelerometer, proximity sensor, and infra-red sensor.

According to some embodiments, the camera microscope, and/or endoscope are configured for imaging of and area surrounding the end effector. According to some embodiments, and as described in greater detail elsewhere herein, the camera microscope, and/or endoscope are positioned along and/or coupled to a portion of the surgical instrument 104. According to some embodiments, the camera microscope, and/or endoscope are positioned along and/or coupled to a portion of the robot arm 102. In some embodiments, the camera microscope, and/or endoscope are in communication with the processor 106. In some embodiments, the processor 106 is configured to receive images from the camera microscope, and/or endoscope.

According to some embodiments, the processor 106 is configured to adjust one or more of the position, orientation, rotation angle, bend angle, and length of at least a portion of the robot arm 102 and/or the surgical instrument 104, based on the image data received from the one or more cameras. According to some embodiments, and as described in greater detail elsewhere herein, the processor 106 is configured to adjust one or more of the position, orientation, rotation angle, bend angle, and length of at least a portion of the robot arm 102 and/or the surgical instrument 104, based on data received by the user and/or from a database.

According to some embodiments, the system 100 comprises a suction channel configured for suction of debris. According to some embodiments, and as described in greater detail elsewhere herein, the surgical instrument 104 comprises the suction channel. According to some embodiments, the suction channel is positioned along a portion of at least one of the surgical instrument 104 and the robotic arm 102.

Surgical Instrument

Figure 2:
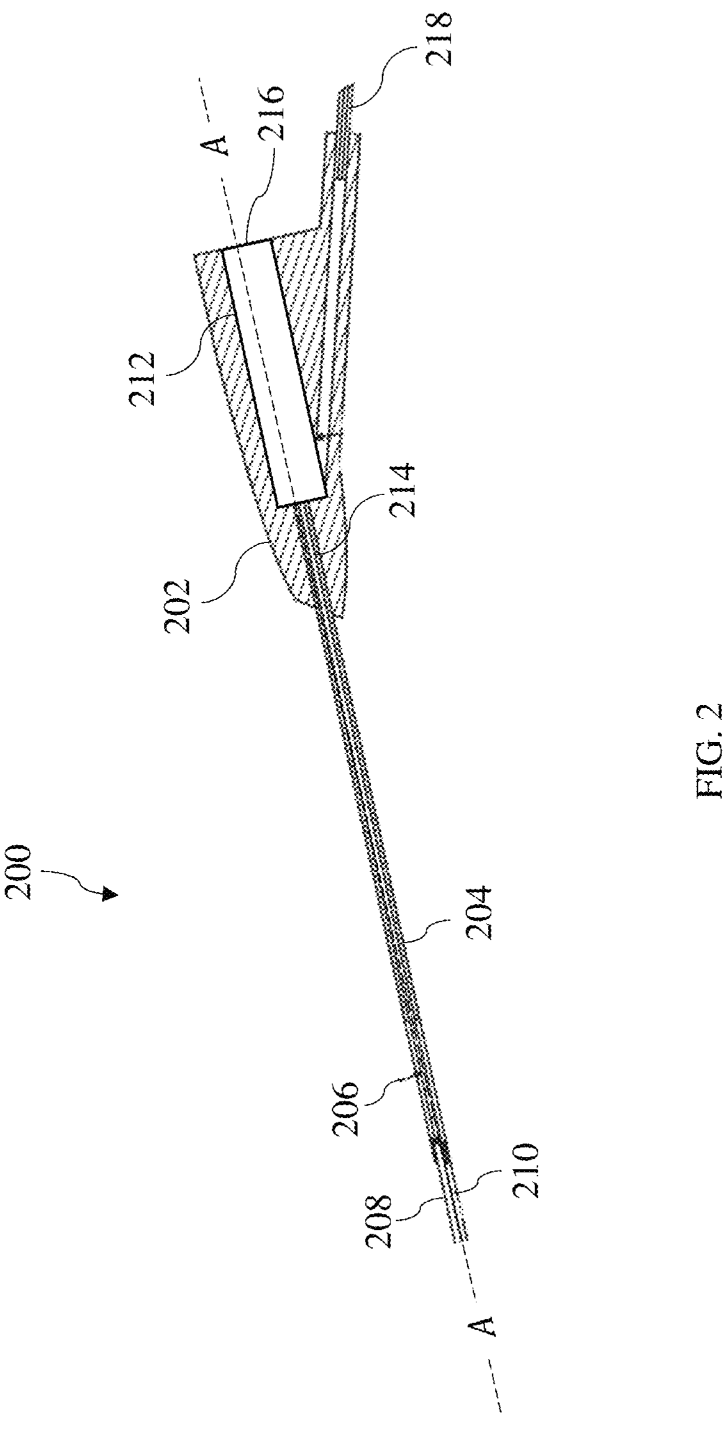
FIG. 2 is a cross sectional view schematic illustration of an exemplary surgical instrument, in accordance with some embodiments of the present invention.

Reference is made to FIG. 2, which a cross sectional view schematic illustration of an exemplary surgical instrument, in accordance with some embodiments of the present invention.

According to some embodiments, the surgical instrument 200/104 comprises a handle 202 coupled to an elongated hollow tubular member 204. According to some embodiments, the surgical instrument 200/104 comprises a flexible drive shaft 206 positionable within the elongated hollow tubular member 204. According to some embodiments, the surgical instrument 200/104 comprises an end effector 208. According to some embodiments, the end effector 208 may include a cutting head. According to some embodiments, the end effector may include a camera. According to some embodiments, the end effector may include an endoscope. According to some embodiments, the end effector may include a suction tip. According to some embodiments, the surgical instrument 200/104 comprises a shield 210 configured to cover at least a portion of the end effector 208.

According to some embodiments, the handle 202 is rigid and/or semi-rigid. According to some embodiments, the handle 202 is configured to couple with a holder 112/114 and/or a robot arm 102. According to some embodiments, the handle 202 is couplable with the elongated hollow tubular member 204. According to some embodiments, the handle 202 is couplable with the elongated hollow tubular member 204. According to some embodiments, at least a portion of the elongated hollow tubular member 204 is configured to fit within a lumen 214 of the handle 202.

According to some embodiments, at least a portion of the elongated hollow tubular member 204 is configured to couple to the actuator, the driving unit, and/or the processor via the lumen 214 of the handle 202. According to some embodiments, the handle 202 comprises a chamber 212 configured to receive an actuator and/or a coupling member such as a cable. According to some embodiments, the chamber 212 extends from the lumen 214 to a proximal end of the handle 202.

According to some embodiments, the chamber 212 comprises at least one opening 216 at the distal end of the handle 201, configured to receive an actuator and/or a coupling member such as a cable coupled to the processor. According to some embodiments, the handle 201 and/or the chamber 212 comprises a second opening 218 configured to receive an actuator and/or a coupling member such as a cable coupled to the processor.

According to some embodiments, the second opening 218 is configured to couple to an actuator and/or a coupling member such as a cable coupled to the processor thereby enabling control of the movement, orientation, and/or rotation of the handle 202. According to some embodiments, the handle 202 is coupled to the driving unit and/or processor via opening 218. According to some embodiments, the handle 202 along a longitudinal axis thereof.

According to some embodiments, the elongated hollow tubular member 204 is rotatable about a longitudinal axis thereof, e.g., axis (A). According to some embodiments, the longitudinal axis of the elongated hollow tubular member 204 and the longitudinal axis of the handle 202 are coaxial and/or parallel. According to some embodiments, the elongated hollow tubular member 204 is rotatable in relation to the handle 202. According to some embodiments, the elongated hollow tubular member 204 is rotatable within the lumen 214. According to some embodiments, the processor is configured to control the orientation of the elongated hollow tubular member 204. According to some embodiments, the orientation of the elongated hollow tubular member 204 is manually controllable via the handle 202. For example, according to some embodiments, the orientation of the elongated hollow tubular member 204 can be controlled by a user, for example, by manipulation of the handle 202.

Reference is made to FIG. 3A, FIG. 3B, FIG. 3C, and FIG. 3D are perspective view schematic illustration of exemplary elongation mechanisms, in accordance with some embodiments of the present invention.

According to some embodiments, the length of the elongated hollow tubular member 204 is adjustable. According to some embodiments, the elongated hollow tubular member 204 is elongatable along a longitudinal axis thereof. According to some embodiments, one or more sections of the elongated hollow tubular member 204 are elongatable along a longitudinal axis thereof. According to some embodiments, the elongated hollow tubular member 204 comprises an elongation mechanism, for example, such as the elongation mechanisms 300/302/304/306 depicted in FIG. 3A, FIG. 3B, FIG. 3C, and FIG. 3D, respectively. According to some embodiments, and as described in greater detail elsewhere herein, the elongation mechanism comprises one or more bending mechanism.

According to some embodiments, the elongation mechanism is configured to enable the adjustability of the length of the elongated hollow tubular member 204. According to some embodiments, the elongated hollow tubular member 204 comprises one or more portions comprising one or more elongation mechanisms. According to some embodiments, the elongated hollow tubular member 204 comprises a cover configured to prevent the elongation mechanism from being exposed.

According to some embodiments, the elongation mechanism comprises any one or more of a net, a mesh, a folded sheet, telescopic elongation mechanism, extension rods and any combination thereof. According to some embodiments, the elongation mechanism comprises a rotatable mechanism, wherein the elongatable portion comprising the elongation mechanism is configured to rotate and/or twist about an axis of elongation of the elongation mechanism. According to some embodiments, the axis of elongation of the elongation mechanism is parallel to and/or coaxial with the longitudinal axis of the elongated hollow tubular member 204.

According to some embodiments, the processor is configured to control the length of the elongated hollow tubular member 204 by controlling the driving unit and/or the elongation mechanism. According to some embodiments, the handle 202 is configured to control the length of the elongated hollow tubular member 204, for example, by manual manipulation of one or more portion of the handle 202.

Elongation Mechanism

Figure 3D:
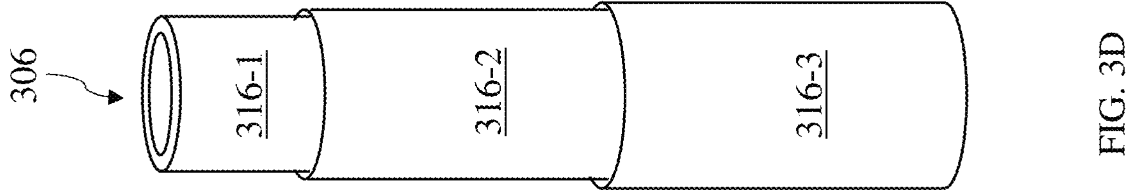
FIG. 3A, FIG. 3B, FIG. 3C, and FIG. 3D are perspective view schematic illustrations of exemplary elongation mechanisms, in accordance with some embodiments of the present invention.
Figure 3C:
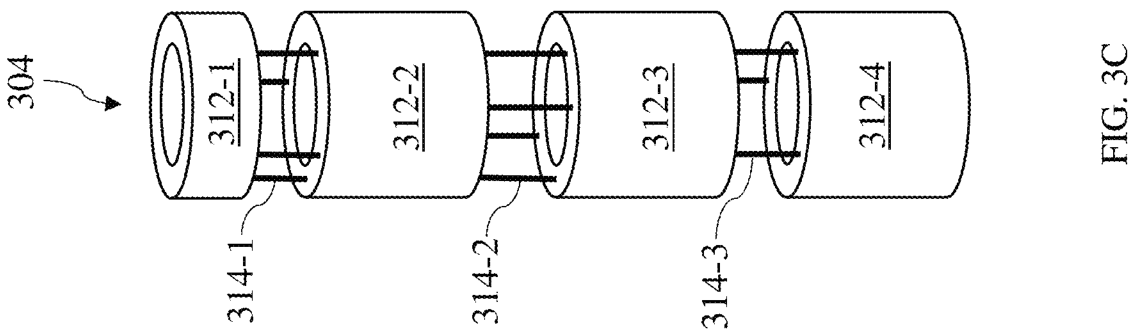
Figure 3B:
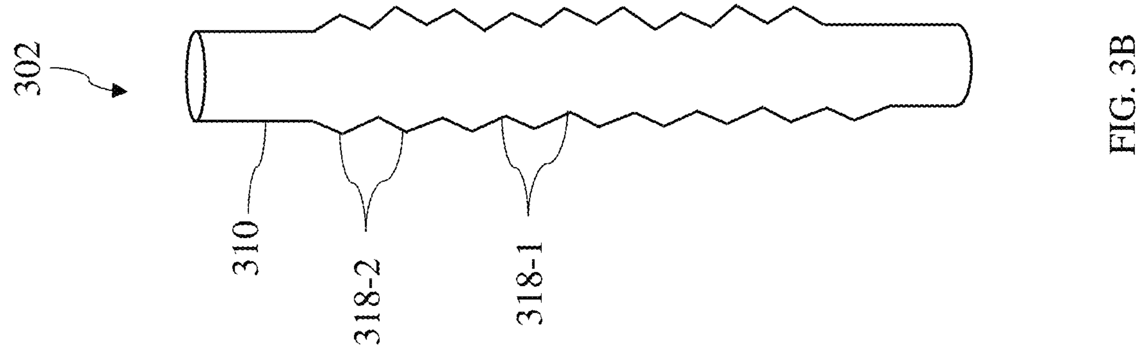
Figure 3A:
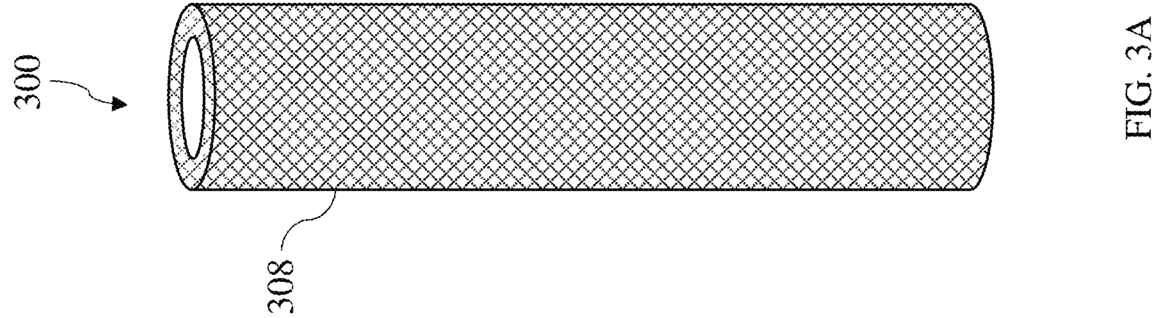

According to some embodiments, such as depicted in FIG. 3A, the elongation mechanism 300 comprises a net 308. According to some embodiments, the net 308 comprises longitudinal supports and latitudinal supports. According to some embodiments, the longitudinal supports and/or the latitudinal supports are rigid and/or semi-rigid. According to some embodiments, the longitudinal supports and latitudinal supports of the net 308 are coupled and/or intertwined. According to some embodiments, the longitudinal supports and the latitudinal supports define apertures therebetween, wherein the apertures comprise an adjustable shape. According to some embodiments, the longitudinal supports and latitudinal supports of the net 308 are moveable in relation to each other, thereby enabling a change of the length along the elongation mechanism 300.

According to some embodiments, such as depicted in FIG. 3B, the elongation mechanism 302 comprises a foldable sheet 310. According to some embodiments, the foldable sheet 310 is rigid and/or semi-rigid. According to some embodiments, the foldable sheet 310 comprises one or more creases 318-1/318-2 (referred to herein as creases 318) about which the sheet 310 is foldable. According to some embodiments, the foldable sheet 310 comprises inner creases 318-1 and/or outer creases 318-2 about which the sheet 310 is foldable. According to some embodiments, at a folded state of the foldable sheet 310, the effective length of the foldable sheet 310 is shorter than the effective length of the foldable sheet 310 at an open and/or partially open state of the foldable sheet 310.

According to some embodiments, such as depicted in FIG. 3C, the elongation mechanism 304 comprises one or more segments 312-1/312-2/312-3/312-4 (referred to herein as one or more segments 312). According to some embodiments, the one or more segments 312 are coupled to each other via a plurality of rods 314-1/314-2/314-3 (referred to herein as rods 314). According to some embodiments, the one or more segments 312 are slidable along the plurality of rods 314. According to some embodiments, the plurality of rods 314 are coupled to each other. According to some embodiments, the distance between the one or more segments 312 is adjustable by sliding the one or more segments 312 along the plurality of rods 314. According to some embodiments, the one or more segments 312 are movable in relation to each other. According to some embodiments, the plurality of rods 314 are fixed in relation to each other.

According to some embodiments, such as depicted in FIG. 3D, the elongation mechanism 306 comprises one or more tubular sheaths 316-1/316-2/316-3 (referred to herein as one or more sheaths 316) fitted to slide in relation to each other along a longitudinal axis thereof. According to some embodiments, the one or more sheaths 316 are coaxial. According to some embodiments, the elongation mechanism 306 is telescopically elongatable by extending one or more sheaths 316 from a closed position to an open position. According to some embodiments, at a closed position, one or more sheaths 316 are positioned within each other. According to some embodiments, at the open position, the one or more sheaths 316 are positioned one after the other. According to some embodiments, at a partially open position, such as depicted in FIG. 3D, the one or more sheaths 316 extend out from each other.

According to some embodiments, the one or more elongation mechanisms are coupled to the processor and/or the driving unit. According to some embodiments, the one or more elongation mechanisms are controllable via the processor and/or the driving unit. According to some embodiments, the processor is configured to command the length of the elongated hollow tubular member 204 by commanding an elongation and/or contraction of the elongation mechanisms. According to some embodiments, the processor is configured to command the driving unit to drive the elongation and/or contraction of the elongation mechanisms.

According to some embodiments, the processor is configured to control the spatial orientation of the elongated hollow tubular member 204 by commanding a change of length of the elongated hollow tubular member 204. According to some embodiments, the processor is configured to control the spatial orientation of the elongated hollow tubular member 204 by commanding a change of angle of rotation of the elongated hollow tubular member 204 in relation to a longitudinal axis thereof, e.g., axis (A) as depicted in FIG. 2.

Bending Mechanism

Figure 4A:
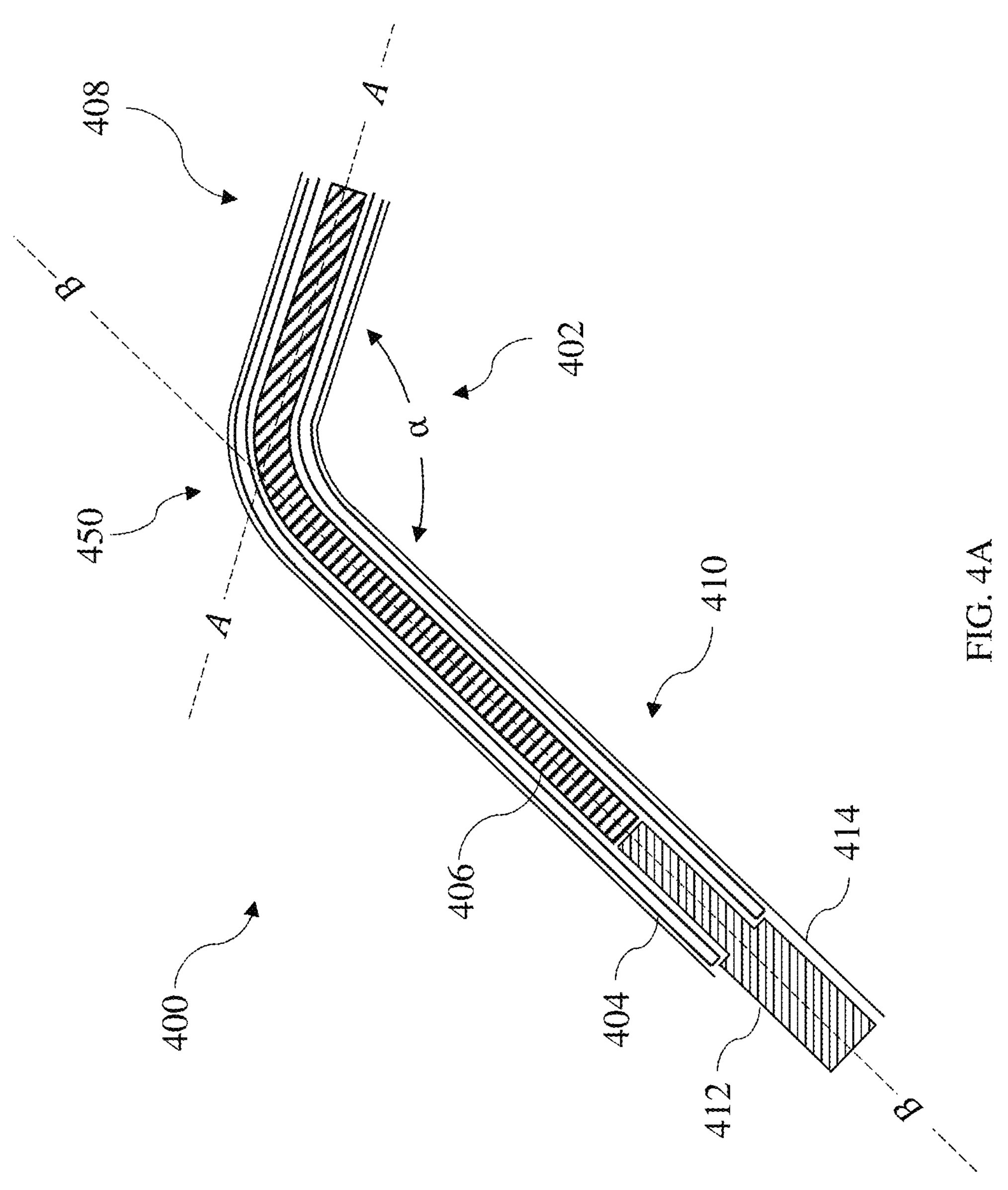
FIG. 4A is a cross sectional view schematic illustration of an exemplary bent portion of an elongated hollow tubular member, in accordance with some embodiments of the present invention.

Reference is made to FIG. 4A, which is a cross sectional view schematic illustration of an exemplary bent portion of an elongated hollow tubular member, in accordance with some embodiments of the present invention.

According to some embodiments, the surgical instrument 400/200/104 and/or elongated hollow tubular member 404/204 comprises one or more bent portion 450. According to some embodiments, the one or more bent portion 450 comprises the elongated hollow tubular member 404/204 and/or the flexible drive shaft 406/206. According to some embodiments, the elongated hollow tubular member 404/204 comprises one or more rigid, semi-rigid, and/or flexible regions at the bent portion 450 of the surgical instrument 400/200/104.

According to some embodiments, the portion of the surgical instrument 400/200/104 positioned between the bent portion 450 and the handle is defined as the proximal portion 408. According to some embodiments, the portion of the surgical instrument 400/200/104 positioned between the bent portion 450 and the end effector 412 is defined as the distal portion 410. According to some embodiments, the end effector 412 may include a cutting head. According to some embodiments, the end effector may include a camera. According to some embodiments, the end effector may be an endoscope. According to some embodiments, the end effector may include a suction tip. According to some embodiments, the angle ($\alpha$) of the bend is defined as the angle between the longitudinal axis (A) of the proximal portion 408 and the longitudinal axis (B) of the distal portion 410. According to some embodiments, the one or more bent portion 450 is bendable and/or adjustable. According to some embodiments, the angle ($\alpha$) of the bend is adjustable.

According to some embodiments, the proximal portion 408 may be moveable in relation to the handle (such as, for example, hand 202 of FIG. 2). According to some embodiments, the proximal portion 408 may be moveable such that the angle of the longitudinal axis (A) of the proximal portion 408 is adjustable in relation to a longitudinal axis of the handle (not shown). In other words, according to some embodiments, the angle of the proximal portion 408 may be adjustable in relation to the handle. According to some embodiments, the proximal portion 408 may be rotatable in relation to the handle.

Figures 4B, 4C:
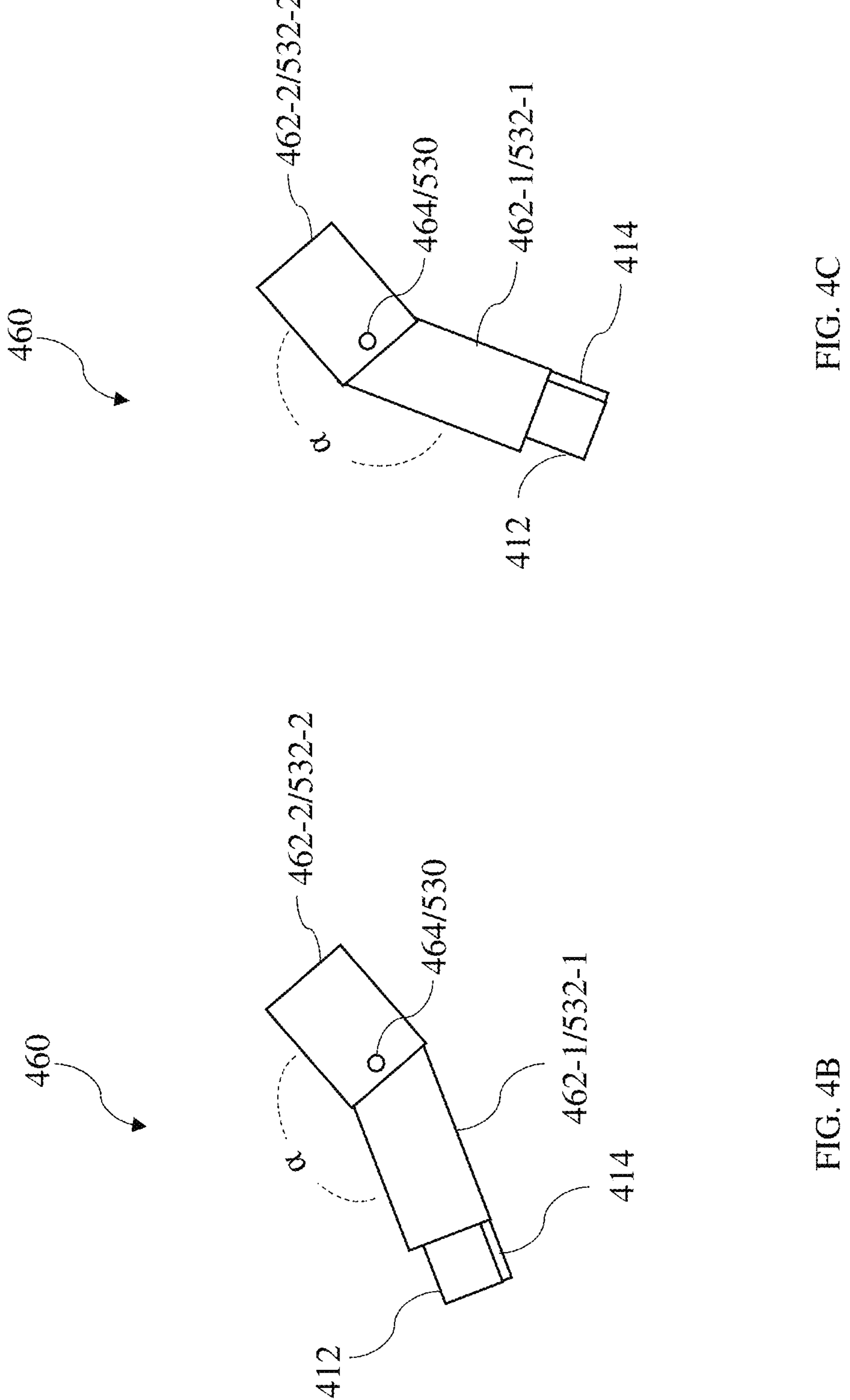
FIG. 4B and FIG. 4C are side view schematic illustrations of an exemplary bent portion of an elongated hollow tubular member, in accordance with some embodiments of the present invention.

Reference is made to FIG. 4B and FIG. 4C, which are side view schematic illustrations of an exemplary bent portion of an elongated hollow tubular member, in accordance with some embodiments of the present invention.

According to some embodiments, such as depicted in FIG. 4B, the angle ($\alpha$) of the bend ranges between 0 and 180 degrees. According to some embodiments, such as depicted in FIG. 4C, the angle ($\alpha$) of the bend ranges between 0 and 360 degrees. According to some embodiments, the angle ($\alpha$) of the bend ranges between 0 and 180 degrees in both a counter clockwise direction and a clockwise direction in relation to the longitudinal axis (A) of the proximal portion 408. A potential advantage of the angle ($\alpha$) of the bend ranging between 0 and 360 degrees is in that the surgical instrument can be used to maneuver the end effector and/or the shield into tissue regions inaccessible within the neuroforamen in the spinal column of the subject.

According to some embodiments, the surgical instrument can be used to maneuver the end effector and/or the shield in real time and/or during surgery. According to some embodiments, the maneuvering includes positioning the surgical instrument at a location in which the shield is used to separate between the tissue and the bone. According to some embodiments, the surgical instrument is configured for maneuvering such that the shield prevents the end effector from damaging tissue and/or nerves, for example, during laminectomy surgery.

According to some embodiments, the one or more bent portions 450 comprise one or more bending mechanisms. According to some embodiments, one or more portions of the elongated hollow tubular member 404/204 comprises the one or more bent portions 450. According to some embodiments, the one or more bending mechanisms are configured to change the angle ($\alpha$) of the bend of the bent portion 450. According to some embodiments, and as described in greater detail elsewhere herein, the one or more bending mechanisms comprise one or more elongation mechanisms. According to some embodiments, the bending mechanism comprises a locked state in which the angle ($\alpha$) of the bend is fixed.

Figures 5A, 5B, 5C, 5D:
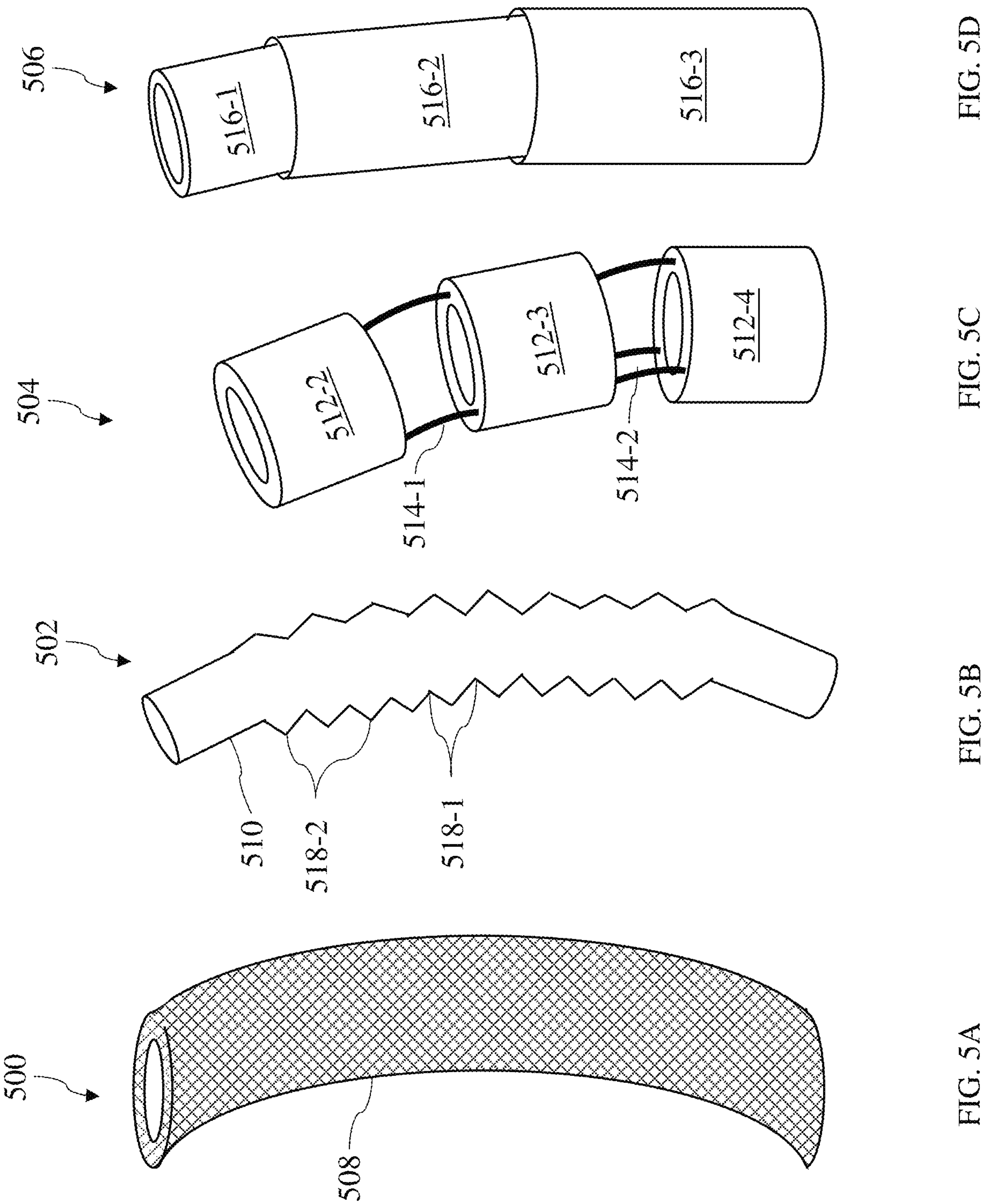

Reference is made to FIG. 5A, FIG. 5B, FIG. 5C, FIG. 5D, FIG. 5E, FIG. 5F and FIG. 5G, which are perspective view schematic illustrations of bending mechanisms, in accordance with some embodiments of the present invention. According to some embodiments, such as depicted in FIG. 5A, the elongation mechanism 500 comprises a net 508/308. According to some embodiments, the net 508/308 is configured to enable tilting of the bent portions 450 and/or the elongated hollow tubular member 404/204 along a longitudinal axis thereof. According to some embodiments, the net 508/308 comprises longitudinal supports and latitudinal supports. According to some embodiments, the longitudinal supports and/or the latitudinal supports are rigid and/or semi-rigid. According to some embodiments, the longitudinal supports and latitudinal supports of the net 508/308 are coupled and/or intertwined. According to some embodiments, the longitudinal supports and the latitudinal supports define apertures therebetween, wherein the apertures comprise an adjustable shape. According to some embodiments, the angles between the longitudinal supports and the latitudinal supports is adjustable. According to some embodiments, the longitudinal supports and latitudinal supports of the net 508/308 are moveable in relation to each other, thereby enabling a change of the angle of the bent portion 450 and/or the elongated hollow tubular member 404/204 along a longitudinal axis thereof.

According to some embodiments, such as depicted in FIG. 5B, the bending mechanism 502 comprises a foldable sheet 510/310. According to some embodiments, the foldable sheet 510/310 is rigid and/or semi-rigid. According to some embodiments, the foldable sheet 510/310 comprises one or more creases 518-1/518-2 (referred to herein as creases 518) about which the sheet 510/310 is foldable. According to some embodiments, the foldable sheet 510/310 comprises one or more inner creases 518-1 and/or outer creases 518-2 about which the sheet 510/310 is foldable. According to some embodiments, the angle formed by the foldable sheet 510/310 around the crease 518 is adjustable, thereby forming a flexible configuration which allows the overall shape of the foldable sheet 510/310 to curve and/or tilt.

According to some embodiments, such as depicted in FIG. 5C, the bending mechanism 504 comprises one or more segments 512-1/512-2/512-3/312-1/312-2/312-3/312-4 (referred to herein as one or more segments 512). According to some embodiments, the one or more segments 512 are coupled to each other via a plurality of rods 514-1/514-2/514-1/314-2/314-3 (referred to herein as rods 514). According to some embodiments, the one or more segments 512 are slidable along the plurality of rods 514. According to some embodiments, the plurality of rods 514 are coupled to each other. According to some embodiments, the one or more rods 514 are semi-rigid and/or flexible. According to some embodiments, the one or more rods 514 are bendable. According to some embodiments, at a bent state of the bending mechanism 504, the one or more segments 512 are tilted in relation to each other. According to some embodiments, at a bent state of the bending mechanism 504, each tilt angle between two of the segments 512 is independent from other tilt angles between other segments 512. According to some embodiments, at a bent state of the bending mechanism 504, the angles of tilt between the one or more segments 512 is the same.

According to some embodiments, such as depicted in FIG. 5D, the bending mechanism 506 comprises one or more tubular sheaths 516-1/516-2/516-3/316-1/316-2/316-3 (referred to herein as one or more sheaths 516) positioned within each other and configured to tilt in relation to each other. According to some embodiments, at an unbent state of the bending mechanism 506, the one or more sheaths 516 are coaxial. According to some embodiments, at a bent state of the bending mechanism 506, the two or more of the sheaths 516 are positioned such that the longitudinal axes of the sheaths are angled in relation to each other. According to some embodiments, the bending mechanism 506 is also telescopically elongatable by extending one or more sheaths 516 from a closed position to an open position, as described in greater detail elsewhere herein.

According to some embodiments, such as depicted in FIG. 5E, the bending mechanism 520 comprises one or more tubular segments having apertures 522. According to some embodiments, the apertures are defined by a frame of the tubular segment, wherein the apertures comprise holes of material that had been removed from the frame of the tubular segment. According to some embodiments, the bending mechanism 520 is manufactured using a laser to cut through the tubular segment, thereby creating the apertures 522.

According to some embodiments, the apertures 522 are circular, oval, polygonal, or any combination thereof. According to some embodiments, the shapes and/or sizes of the apertures 522 vary. According to some embodiments, the shapes and/or sizes of the apertures 522 vary along a length of the tubular segment. According to some embodiments, the shapes and/or sizes of the apertures 522 vary along a length of the tubular segment such that the tubular segment is bent at a specific portion thereof and/or in accordance with a type, value, and/or vector of a force applied thereto. For example, according to some embodiments, the tubular segment comprises a middle portion positioned essentially in the middle of the length of the tubular segment, wherein the sizes of the apertures 522 along the middle portion is different than the sizes of the apertures 522 on either end of the middle portion.

According to some embodiments, such as depicted in FIG. 5F, the bending mechanism 524 comprises one or more tubular segments having slots 526. According to some embodiments, each of the slots 526 comprise opposing inner walls. According to some embodiments, the inner walls of the slots 526 extend within at least a portion of a thickness of the wall of the tubular segment. According to some embodiments, at an open position, the opposing inner walls of the slots 526 are distanced from one another. According to some embodiments, at a bent position of the bending mechanism 524, the opposing inner walls of the slots 526 are abutting. According to some embodiments, the opposing inner walls of the slots 526 form a triangular and/or conical cavity within a wall of the tubular segment of the bending mechanism 524. According to some embodiments, such as depicted in FIG. 5G, the bending mechanism 528 comprises one or more hinges 530. According to some embodiments, the bending mechanism 528 comprises two or more segments 532-1/532-2 (referred to herein as segments 532). According to some embodiments, the two or more segments 532 are coupled by the one or more hinges 530. According to some embodiments, the angle between a first segment 532-1 and a second segment 532-2 defines the angle ($\alpha$) of the bend.

According to some embodiments, the bending mechanism comprises a bendable axis positioned along a length of the bent portion 450. According to some embodiments, the bendable axis is coupled to the bent portion such that a movement and/or change in spatial orientation of the bendable axis, the angle ($\alpha$) of the bend is adjusted. According to some embodiments, the bendable axis comprises a rod and/or a wire. According to some embodiments, the bendable axis is operated by a lever. According to some embodiments, the lever is positioned in the handle.

According to some embodiments, the one or more bending mechanisms are coupled to the processor and/or the driving unit. According to some embodiments, the one or more bending mechanisms are controllable via the processor and/or the driving unit. According to some embodiments, the processor is configured to command the angle ($\alpha$) of bend of the bended portion 450 by controlling the one or more bending mechanism. According to some embodiments, the processor is configured to command the driving unit to drive the angle of the bend of the bending mechanism. According to some embodiments, the processor is configured to control the spatial orientation of the elongated hollow tubular member 204 by commanding a change of the angle ($\alpha$) of the bend of the bent portion 450.

According to some embodiments, the one or more bending mechanisms are coupled to the handle 202. According to some embodiments, the one or more bending mechanisms are manually controllable via the handle 202. According to some embodiments, the handle 202 is configured for manual control of the angle ($\alpha$) of bend of the bent portion.

Flexible Drive Shaft

According to some embodiments, the surgical instrument 400/200/104 comprises the flexible drive shaft 406/206 shaft positioned within the elongated hollow tubular member 404/204. According to some embodiments, the flexible drive shaft 406/206 is coupled to the end effector 412/208 at a distal end of the flexible drive shaft 406/206. According to some embodiments, the flexible drive shaft 406/206 is coupled to one or more of the handle, the driving unit, and the elongated hollow tubular member 404/204 at a proximal end of the flexible drive shaft 406/206.

According to some embodiments, the flexible drive shaft 406/206 is configured to transfer torque and rotational speed of at least 10,000 rpm, from a proximal end of the elongated hollow tubular member 404/204 to the end effector 412/208. According to some embodiments, the flexible drive shaft 406/206 is configured to transfer torque and rotational speed of at least 10,000 rpm, from a proximal end of the elongated hollow tubular member 404/204 to the end effector 412/208 regardless of the angle (α) of the bend of the surgical instrument 400/200/104 and/or the bent portion 450. According to some embodiments, the flexible drive shaft 406/206 is configured to transfer torque and rotational speed of at least 10,000 rpm, from a proximal end of the elongated hollow tubular member 404/204, through the bent portion 450, to the end effector 412/208. According to some embodiments, the rotation may be continuous rotation. According to some embodiments, the rotation may be reciprocal rotation.

According to some embodiments, the flexible drive shaft 206/406 comprises a core made of a plurality of stranded or braided wires and at least one outer layer comprising a layer of wires wound around the core. According to some embodiments, the core of the flexible drive shaft 406/206 is configured to transfer at least a portion of the torque from the driving unit to the end effector 412/208. According to some embodiments, the surgical instrument 400/200/104 comprises one or more torque transfer elements connected to the flexible drive shaft 406/206.

Advantageously, the flexible drive shaft 206/406 and/or the one or more torque transfer elements enable the surgical instrument 400/200/104 to operate at a fixed position for a prolonged period of time, transferring torque to the end effector 412/208, thereby increasing the safety of the procedure, e.g. due to a minimized risk of damaging nerves within or proximal to the surgical site. According to some embodiments, the one or more torque elements are integral with the flexible drive shaft 406/206. According to some embodiments, the one or more torque elements comprise one or more bending mechanism.

Figure 6:
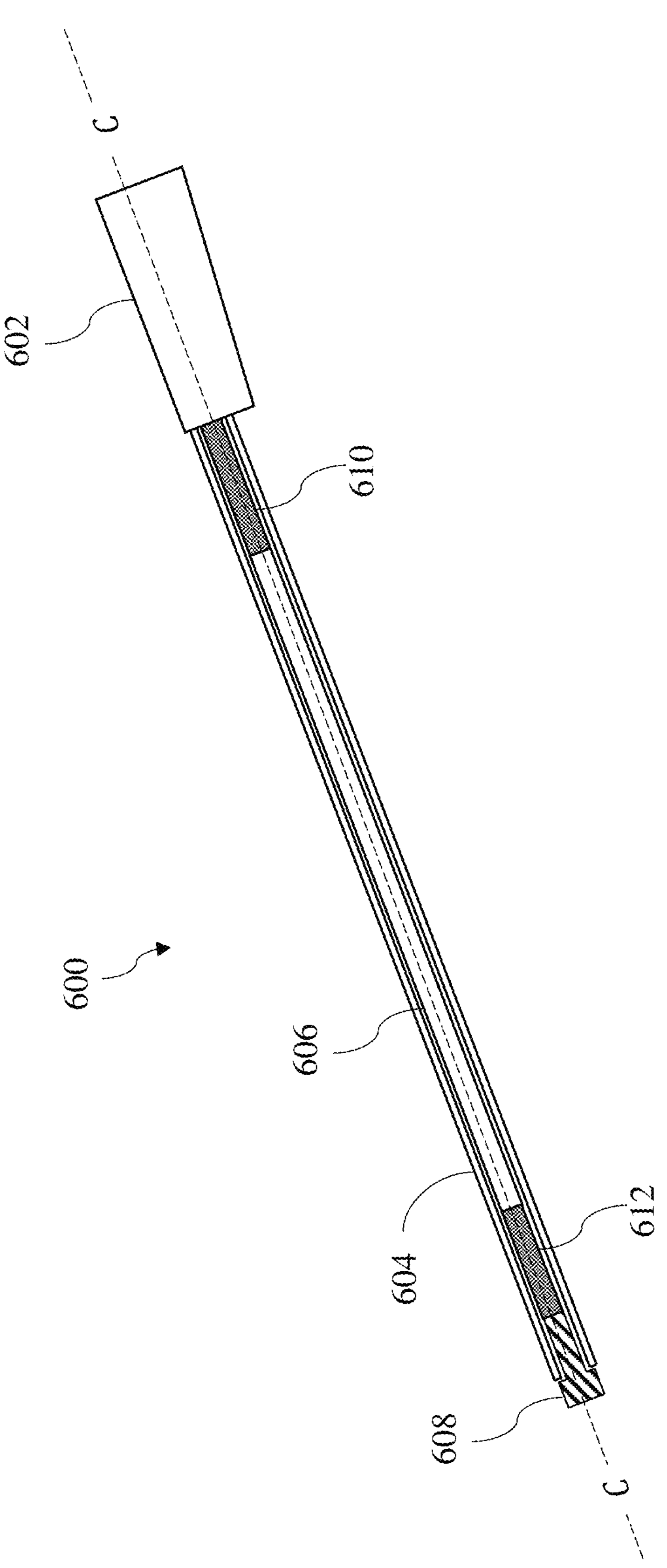
FIG. 6 is a cross sectional view schematic illustration of an exemplary surgical instrument, in accordance with some embodiments of the present invention.
Figure 6:

Reference is made to FIG. 6, which is a cross sectional view schematic illustration of an exemplary surgical instrument, in accordance with some embodiments of the present invention.

According to some embodiments, the surgical instrument 600/400/200/104 comprises a proximal torque transfer element 610 positioned within the elongated hollow tubular member 604/404/204 and coupled to a proximal end of the flexible drive shaft 606/406/206. According to some embodiments, the proximal torque transfer element 610 is coupled to the driving unit and/or the handle at one end and to the flexible drive shaft 606/406/206 at a second end.

According to some embodiments, the surgical instrument 600/400/200/104 comprises a distal torque transfer element 612 positioned within the elongated hollow tubular member 604/404/204 and coupled to a distal end of the flexible drive shaft 606/406/206. According to some embodiments, distal torque transfer element 612 is coupled to the end effector 608/412/208 at one end and to the flexible drive shaft 606/406/206 at a second end.

According to some embodiments, the one or more torque transfer elements are elongatable along the longitudinal axis (C) thereof. According to some embodiments, the one or more torque transfer elements comprise an elongation mechanism, such as, for example, the one or more of the elongation mechanisms 300/302/304/306. According to some embodiments, the proximal and/or distal torque transfer elements 610/612 are independently elongatable. According to some embodiments, the proximal and/or distal torque transfer elements 610/612 elongatable via one or more elongation mechanism, such as, for example, the elongation mechanism 300/302/304/306.

According to some embodiments, the proximal and/or distal torque transfer elements 610/612 are coupled to the processor and/or the driving unit. According to some embodiments, the proximal and/or distal torque transfer elements 610/612 are controllable via the processor and/or the driving unit. According to some embodiments, the processor is configured to command the elongation and/or contraction of the proximal and/or distal torque transfer elements 610/612. According to some embodiments, and as described in greater detail elsewhere herein, different portions of the surgical instrument 600/400/200/104, the elongated hollow tubular member 604/404/204, the flexible drive shaft 606/406/206, the proximal torque transfer element 610, and the distal torque transfer element 610 comprises one or more of elongation mechanism 300/302/304/306. and/or one or more bending mechanism 500/502/504/506/520/524/528. According to some embodiments, the position of the bent portion 450 changes in relation to one or more of the handle 202 of the surgical instrument 600/400/200/104 and the end effector 608/412/208. According to some embodiments, the position of the bent portion 450 changes during elongation and/or contraction of one or more portions of the surgical instrument 600/400/200/104.

End Effector

According to some embodiments, the end effector may include one or more of a cutting head, a camera, and a suctioning tip, or any combination thereof.

According to some embodiments, the end effector may be a cutting head. According to some embodiments, the end effector may be configured for cutting and/or removing tissue. According to some embodiments, the end effector may be configured for manipulating tissue. According to some embodiments, the end effector may be a camera. According to some embodiments, the end effector may be an endoscope.

According to some embodiments, the end effector may be a suction tip. According to some embodiments, the end effector may be configured for suctioning fluids from a cavity within a body of the subject. According to some embodiments, the surgical instrument 600/400/200/104 and/or the surgical instrument 600/400/200/104 may include a lumen therein, configured for removal of fluids suctioned by the suctioning tip.

Figures 7A, 7B:
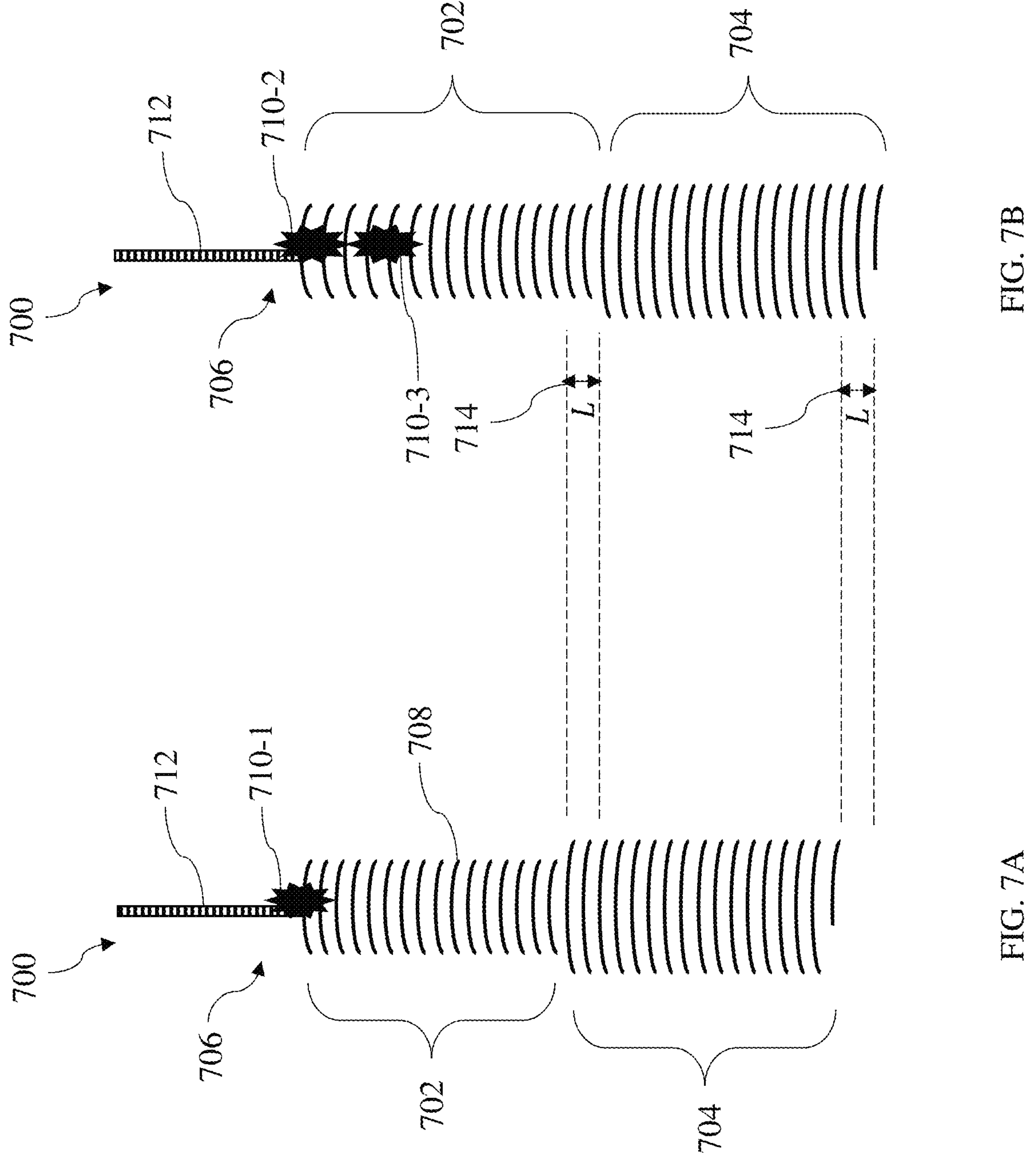
FIG. 7A and FIG. 7B are cross sectional view schematic illustrations of an exemplary elongatable end effector at a contracted state and an elongated state, respectively, in accordance with some embodiments of the present invention.

Reference is made to FIG. 7A and FIG. 7B, which are cross sectional view schematic illustrations of an exemplary elongatable end effector at a contracted state and an elongated state, respectively, in accordance with some embodiments of the present invention.

According to some embodiments, the end effector 700/608/412/208 may be a cutting head. According to some embodiments, the end effector 700/608/412/208 comprises a proximal portion 702 and a distal portion 704. According to some embodiments, the proximal portion 702 of the end effector 700/608/412/208 is configured to fit within the elongated hollow tubular member 604/404/204. According to some embodiments, the proximal portion 702 of the end effector 700/608/412/208 is coupled to one or more of the flexible drive shaft 606/406/206 and the distal torque transfer element 612. According to some embodiments, the proximal portion 702 of the end effector 700/608/412/208 is coupled to or is a unit with the distal portion 704 of the end effector 700/608/412/208. According to some embodiments, the distal portion 704 of the end effector 700/608/412/208 is configured to extend from the elongated hollow tubular member 604/404/204. According to some embodiments, the distal portion 704 of the end effector 700/608/412/208 and/or the cutting head is configured for cutting tissue. According to some embodiments, the distal portion 704 of the end effector 700/608/412/208 is configured for any one or more of cutting the tissue, manipulating the tissue, suctioning fluids from the vicinity of the tissue, and enabling a user to observe the tissue.

According to some embodiments, the end effector 700/608/412/208 is extendable from the elongated hollow tubular member 604/404/204. According to some embodiments, the end effector 700/608/412/208 is contractable into the elongated hollow tubular member 604/404/204. According to some embodiments, the end effector 700/608/412/208 is slidable within the elongated hollow tubular member 604/404/204. According to some embodiments, at least one of the proximal portion 702 and the distal portion 704 are elongatable.

According to some embodiments, the length of the end effector 700/608/412/208 is adjustable. According to some embodiments, the length of the proximal portion 702 and/or the distal portion 704 is individually adjustable. According to some embodiments, one or more of the proximal portion 702 and the distal portion 704 comprises an elongation mechanism, such as, for example, the elongation mechanism 300/302/304/306.

According to some embodiments, one or more of the proximal portion 702 and the distal portion 704 comprises an elongation mechanism 706, such as depicted by FIG. 7A and FIG. 7B. According to some embodiments, the elongation mechanism 706 comprises one or more gears 710-1/710-2/710-3 (referred to herein as one or more gears 710) are configured to slide between one or more cutting sections 708 of the cutting head and/or the end effector 700/608/412/208. According to some embodiments, the one or more cutting sections 708 may include a configuration and/or a composition configured to cut through a designated tissue, such as, for example, the excess bone tissue.

According to some embodiments, the proximal portion 702 and/or the distal portion 704 comprise the one or more cutting sections 708 of the cutting head and/or the end effector 700/608/412/208. According to some embodiments, the one or more cutting sections 708 comprise a plurality of cutting edges. According to some embodiments, the one or more cutting sections 708 are a part of a coiling cutting blade. According to some embodiments, the one or more cutting sections 708 is rigid and/or semi-rigid. According to some embodiments, the hardness of the one or more gears 710 is essentially the same or smaller than the hardness of the one or more cutting sections 708 of the cutting head and/or the end effector 700/608/412/208.

According to some embodiments, the one or more gears 710 comprise a plurality of teeth configured to fit between the one or more cutting sections 708. According to some embodiments, the width of the plurality of teeth of the one or more gears 710 is bigger than the original distance between the one or more cutting sections 708. According to some embodiments, the plurality of teeth of the one or more gears 710 are configured to wedge between the one or more cutting sections 708. According to some embodiments, the plurality of teeth of the one or more gears 710 are configured to increase the pitch of the coiling cutting blade by increasing the distance between the one or more cutting sections 708.

According to some embodiments, the elongation mechanism 706 comprises a plurality of gears wherein the width of the teeth of the plurality of gears 710 is varying and/or the same in relation to width of teeth of other gears 710. According to some embodiments, the elongation mechanism 706 comprises a plurality of gears 710 wherein the width of the teeth of the gears 710 are essentially the same as the original distance between the one or more cutting sections 708, thereby providing a stabilizing effect to the cutting head and/or the end effector 700/608/412/208. According to some embodiments, the elongation mechanism 706 comprises a plurality of gears 710 wherein the width of the teeth of the gears 710 are varying, thereby enabling a different range of distances between different portion of the cutting head and/or the end effector 700/608/412/208 and/or different distances between different cutting sections 708 of the cutting head and/or the end effector 700/608/412/208.

According to some embodiments, the elongation mechanism 706 comprises one or more rails 712, wherein the one or more gears 710 are moveable along the one or more rails 712. According to some embodiments, the one or more rails 712 are positioned along a length of the cutting head and/or the end effector 700/608/412/208, a length of the distal portion 704 of the cutting head and/or the end effector 700/608/412/208, a length of a proximal portion 702 of the cutting head and/or the end effector 700/608/412/208, and/or a length between the distal portion 704 and the proximal portion 702 of the cutting head and/or the end effector 700/608/412/208.

According to some embodiments, the cutting head and/or the end effector 700/608/412/208 comprises a plurality of rails 712 distributed about a circumference thereof. According to some embodiments, the one or more rails 712 are positioned within an inner portion of the cutting head and/or the end effector 700/608/412/208. According to some embodiments, the one or more rails 712 are positioned along an inner circumference of the cutting head and/or the end effector 700/608/412/208 and/or cutting sections 708.

According to some embodiments, one or more of the gears 710 and the rails 712 of the elongation mechanism 706 are coupled to the processor and/or the driving unit. According to some embodiments, one or more of the gears 710 and the rails 712 of the elongation mechanism 706 are individually coupled to the processor and/or the driving unit. According to some embodiments, the elongation mechanism 706 is controllable via the processor and/or the driving unit.

According to some embodiments, the processor is configured to command the length L 714 of elongation of the cutting head and/or the end effector 700/608/412/208 by commanding an elongation and/or contraction of the elongation mechanism 706. According to some embodiments, the length L 714 of elongation of the cutting head and/or the end effector 700/608/412/208 is defined as the difference between the length of the cutting head at a contracted state (e.g., FIG. 7A) and the length of the cutting head at an elongated state (e.g., FIG. 7B). According to some embodiments, the processor is configured to command the driving unit to drive the elongation and/or contraction of the elongation mechanism 706. According to some embodiments, the position of the cutting head and/or the end effector 700/608/412/208 in relation to the shield and/or to the elongated hollow tubular member 604/404/204 is adjustable. According to some embodiments, the cutting head and/or the end effector 700/608/412/208 is extendable from the elongated hollow tubular member 604/404/204. According to some embodiments, the cutting head and/or the end effector 700/608/412/208 is contractable into the elongated hollow tubular member 604/404/204. According to some embodiments, at a fully contracted state, the entire cutting head and/or the end effector 700/608/412/208 is positioned within the elongated hollow tubular member 604/404/204.

Figures 8A, 8B:
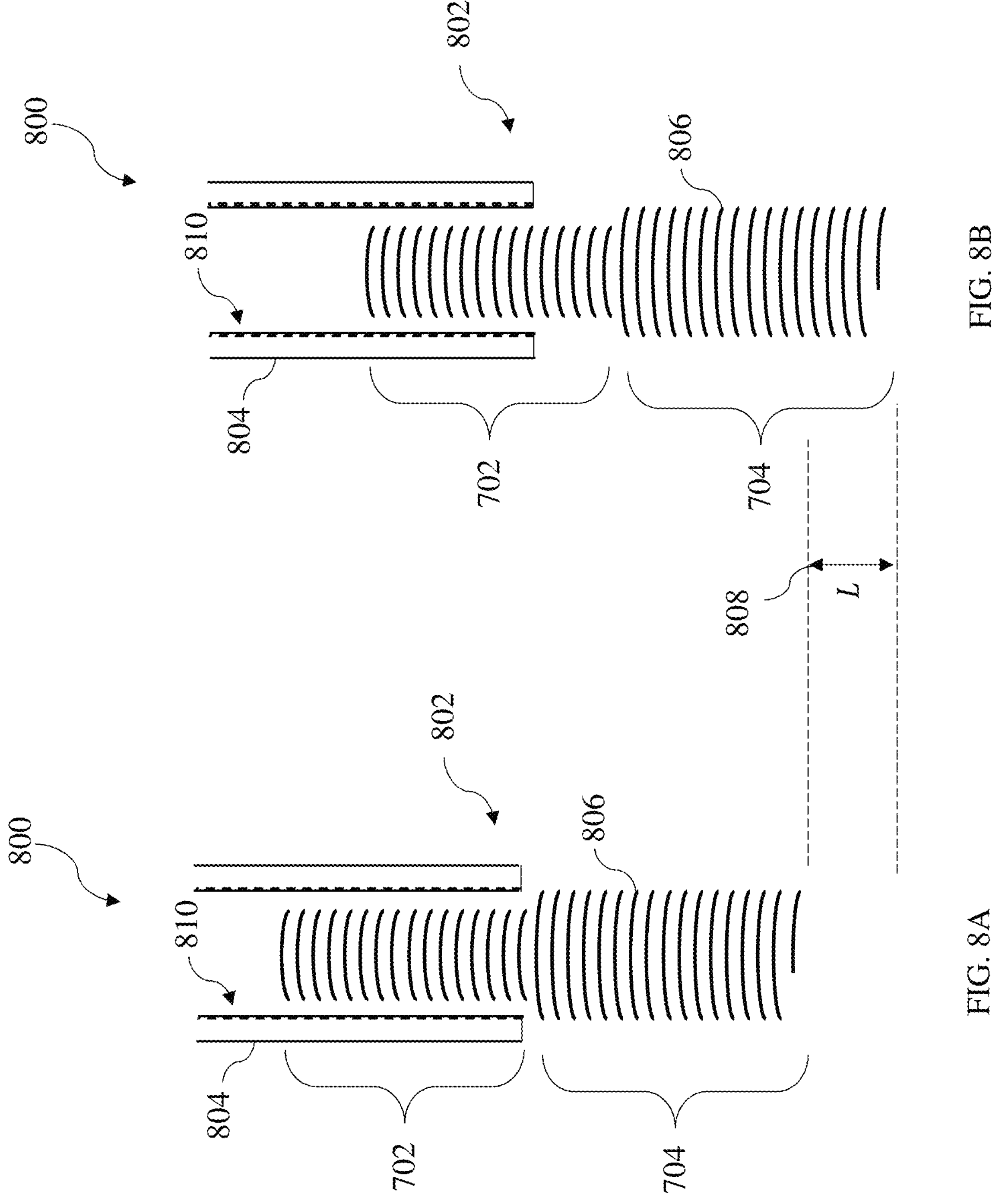
FIG. 8A and FIG. 8B are cross sectional view schematic illustrations of an exemplary elongatable end effector at a contracted state and an elongated state, respectively, in accordance with some embodiments of the present invention.

Reference is made to FIG. 8A and FIG. 8B, which are cross sectional view schematic illustrations of an exemplary elongatable end effector at a contracted state and an elongated state, respectively, in accordance with some embodiments of the present invention.

According to some embodiments, the end effector 800/700/608/412/208 comprises an elongation mechanism 802 comprising a housing 804 and a cutting section 806. According to some embodiments, the housing 804 is coupled able to at least one of the elongated hollow tubular member 604/404/204, the flexible drive shaft 606/406/206 and the distal torque transfer element 612. According to some embodiments, the housing 804 comprises a rail and/or a threaded lumen 810. According to some embodiments, the proximal portion 702 and/or the distal portion 704 of the end effector 800/700/608/412/208 are configured to move along a length of the housing 804 and/or in relation to the housing 804.

According to some embodiments, the elongation mechanism 802 comprises a gear positioned between the housing 804 and the proximal portion 702 and/or the distal portion 704 of the end effector 800/700/608/412/208, such that rotation of the gear correlates with a movement of the proximal portion 702 and/or the distal portion 704 of the end effector 800/700/608/412/208 in relation to the housing 804.

According to some embodiments, the elongation mechanism 802 comprises a threaded portion of the lumen 810 of the housing 804. According to some embodiments, the proximal portion 702 and/or the distal portion 704 of the end effector 800/700/608/412/208 are configured to rotate within the threaded portion of the lumen 810 of the housing 804.

According to some embodiments, one or more of the housing 804, the proximal portion 702 and/or the distal portion 704 of the end effector 800/700/608/412/208 are coupled to the processor and/or the driving unit. According to some embodiments, one or more of the housing 804, the proximal portion 702 and/or the distal portion 704 of the end effector 800/700/608/412/208 are individually coupled to the processor and/or the driving unit. According to some embodiments, the elongation mechanism 802 is controllable via the processor and/or the driving unit.

According to some embodiments, the processor is configured to command a change in the length L 808 of elongation of the end effector 800/700/608/412/208 by commanding an elongation and/or contraction of the elongation mechanism 802. According to some embodiments, the length L 808 of elongation of the end effector 800/700/608/412/208 is defined as the difference between the length of the end effector 800/700/608/412/208 at a contracted state (e.g., FIG. 8A) and the length of the end effector 800/700/608/412/208 at an elongated state (e.g., FIG. 8B). According to some embodiments, the processor is configured to command the driving unit to drive the elongation and/or contraction of the elongation mechanism 802.

Figures 8C, 8D:
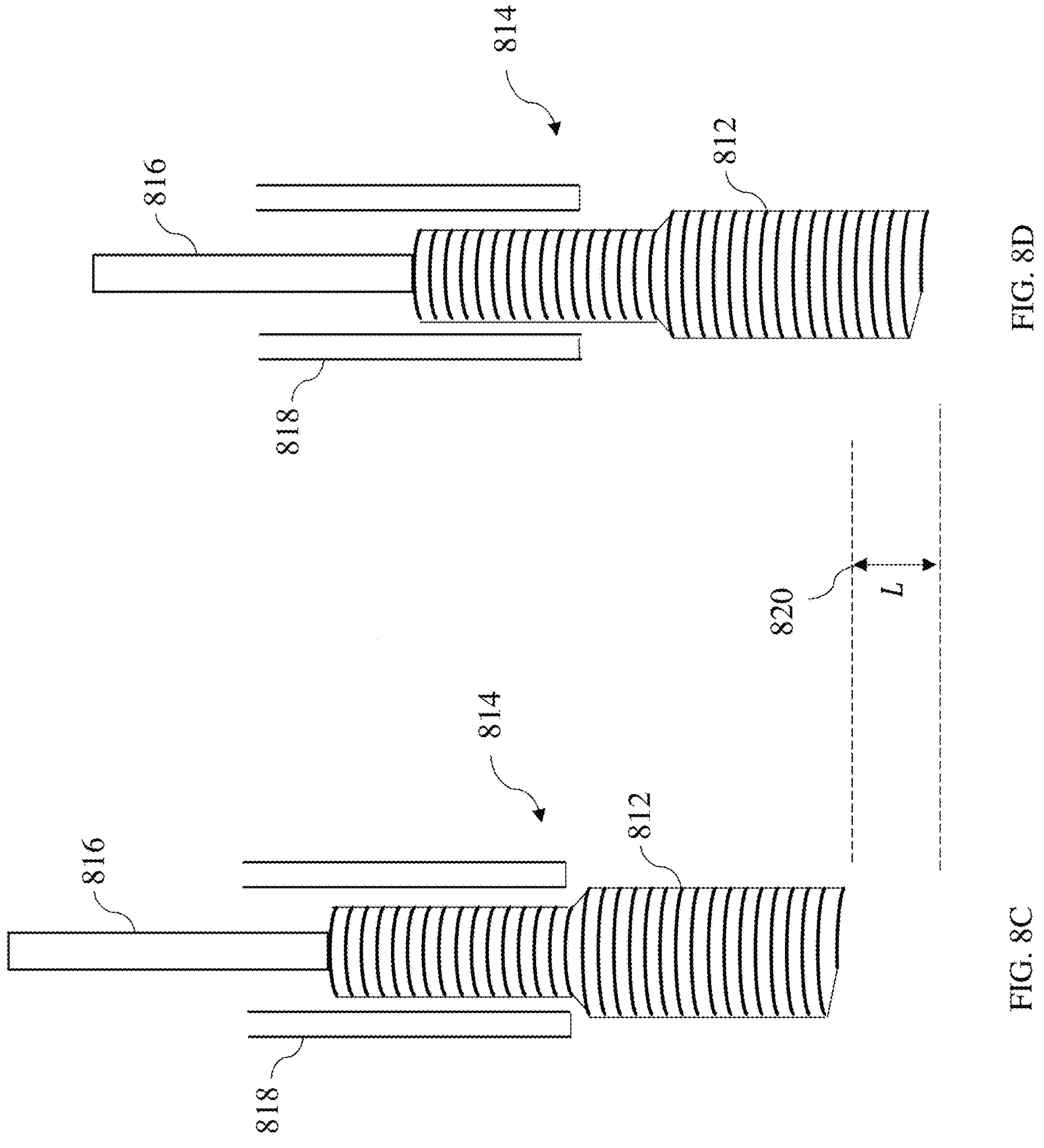
FIG. 8C and FIG. 8D are cross sectional view schematic illustrations of an exemplary elongatable end effector at a contracted state and an extended state, respectively, in accordance with some embodiments of the present invention.

Reference is made to FIG. 8C and FIG. 8D, which are cross sectional view schematic illustrations of an exemplary elongatable cutting head at a contracted state and an extended state, respectively, in accordance with some embodiments of the present invention.

According to some embodiments, the end effector 812/800/700/608/412/208 comprises an extension mechanism 814 comprising an actuator 816. According to some embodiments, the actuator 816 is coupled to at least one of the elongated hollow tubular member 818/604/404/204, the flexible drive shaft 606/406/206 and the distal torque transfer element 612 at one end of the actuator 816. According to some embodiments, the actuator 816 is coupled to the end effector 812/800/700/608/412/208 at a second end of the actuator 816.

According to some embodiments the actuator 816 is configured to elongate and/or contract. According to some embodiments, the actuator 816 comprises a piston. According to some embodiments, the actuator 816 comprises a hydraulic piston. According to some embodiments, elongation and/or contraction of the actuator 816 changes the position of the end effector 812/800/700/608/412/208 in relation to the elongated hollow tubular member 818/604/404/204.

According to some embodiments the actuator 816 comprises an elongated rod. According to some embodiments, the actuator 816 is coupled to the handle of the surgical instrument at one end of the actuator 816. According to some embodiments, the actuator 816 is coupled to the end effector 812/800/700/608/412/208 at a second end of the actuator 816 such that a movement of the actuator 816 in relation to the elongated hollow tubular member 818/604/404/204 translates a position of the end effector 812/800/700/608/412/208 in relation to the elongated hollow tubular member 818/604/404/204. According to some embodiments, the end effector 812/800/700/608/412/208 and the actuator 816 are rigidly coupled.

According to some embodiments, the processor is configured to command a change in the length L 820 of elongation of the end effector 812/800/700/608/412/208 by commanding an extension and/or contraction of the elongation mechanism 814. According to some embodiments, the length L 820 of extension of the end effector 812/800/700/608/412/208 is defined as the difference between the length of the cutting head at a contracted state (e.g., FIG. 8C) and the length of the cutting head at an extended state (e.g., FIG. 8D). According to some embodiments, the processor is configured to command the driving unit to drive the actuator 816 of the elongation mechanism 802. According to some embodiments, the actuator 816 of the elongation mechanism 802 is controllable via the handle of the surgical instrument. According to some embodiments, the actuator 816 of the elongation mechanism 802 is manually controllable via the handle of the surgical instrument.

According to some embodiments, the elongation, extension, and/or contraction of the end effector 812/800/700/608/412/208 in relation to the elongated hollow tubular member 818/604/404/204 is independent from other adjustable portions of the surgical instrument. For example, in some embodiments, the surgical instrument may be implemented by first adjusting a length and/or angle of bend (a) of the elongated hollow tubular member 818/604/404/204 and then extending the cutting head away from the elongated hollow tubular member 818/604/404/204. Shield According to some embodiments, the surgical instrument 600/400/200/104 comprises one or more shields 210/414. According to some embodiments, the one or more shields 210/414 are configured to cover a portion of the end effector 800/700/608/412/208. According to some embodiments, the one or more shields are coupled to the elongated hollow tubular member 604/404/204.

According to some embodiments, the one or more shields 210/414 comprise a curved member wherein the curvature of the shield is essentially coaxial with the elongated hollow tubular member 604/404/204. According to some embodiments, the one or more shields circumferentially extend along a circumference of the elongated hollow tubular member 604/404/204. For example, according to some embodiments, the surgical instrument 600/400/200/104 comprises one shield extending along 180 degrees of the circumference of the elongated hollow tubular member 604/404/204. For example, according to some embodiments, the surgical instrument 600/400/200/104 comprises two shields, each of which is extending along 180 degrees of the circumference of the elongated hollow tubular member 604/404/204.

According to some embodiments, the shield is coupled to the elongated hollow tubular member 604/404/204 at an inner surface of the elongated hollow tubular member 604/404/204, an outer surface of the elongated hollow tubular member 604/404/204, and/or within a thickness of a wall of the elongated hollow tubular member 604/404/204.

According to some embodiments, the one or more shields 210/414 are elongatable along a longitudinal axis thereof and/or a longitudinal axis of the elongated hollow tubular member 604/404/204. According to some embodiments, the one or more shield are elongatable along the direction parallel to the circumference of the elongated hollow tubular member 604/404/204. According to some embodiments, the one or more shields 210/414 comprises an elongation mechanism, such as, for example, the elongation mechanisms 300/302/304/306/500/706/802.

According to some embodiments, the one or more shields 210/414 are extendable along a longitudinal axis thereof and/or a longitudinal axis of the elongated hollow tubular member 604/404/204.

Figures 9A, 9B, 10A:
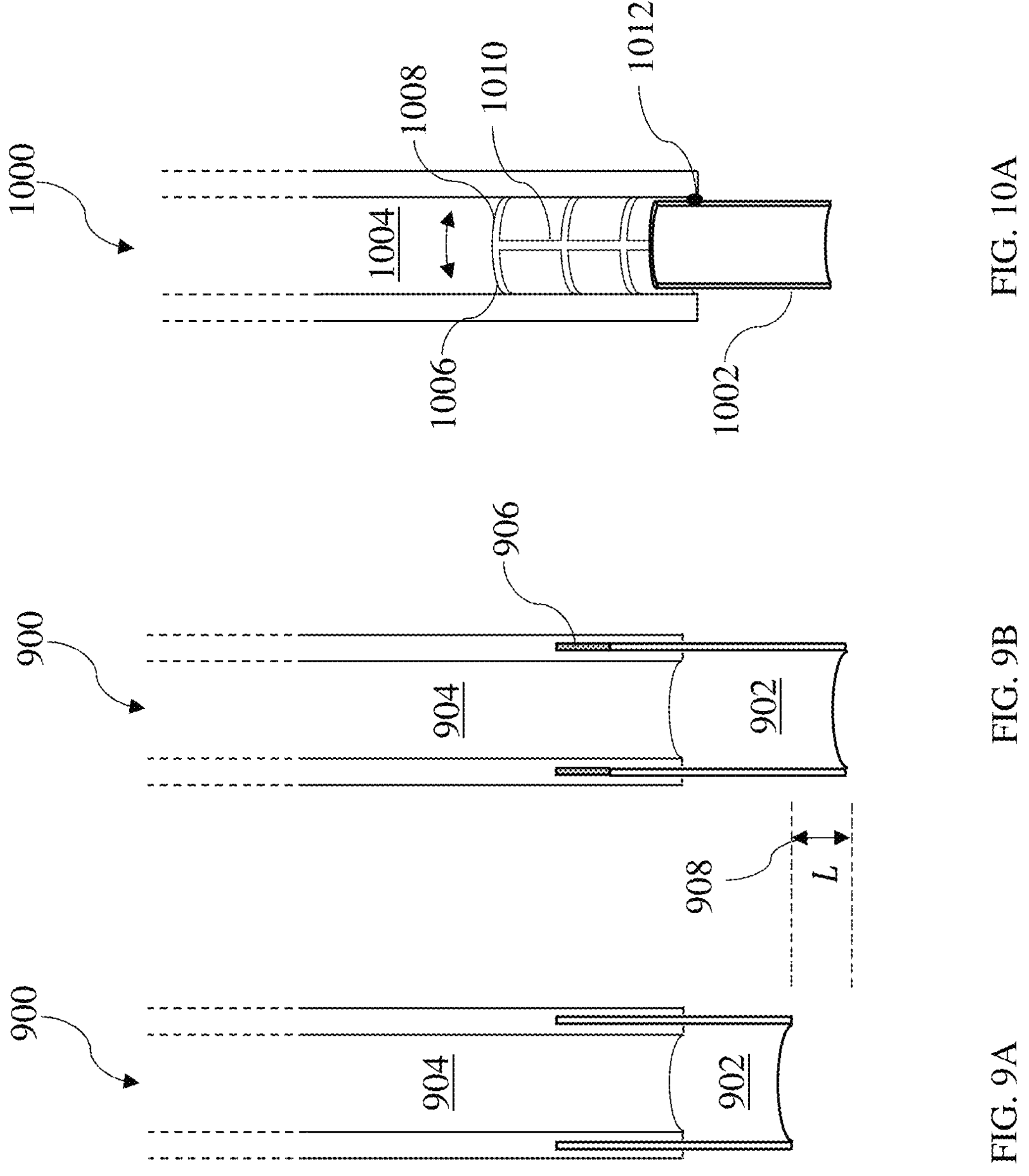
FIG. 9A and FIG. 9B are cross sectional view schematic illustrations of an exemplary extendable shield at a contracted state and an extended state, respectively, in accordance with some embodiments of the present invention.
FIG. 10A is a cross sectional view schematic illustration of an exemplary rotation and extension mechanism of a shield, in accordance with some embodiments of the present invention.

Reference is made to FIG. 9A and FIG. 9B, which are cross sectional view schematic illustrations of an exemplary extendable shield at a contracted state and an extended state, respectively, in accordance with some embodiments of the present invention.

According to some embodiments, the one or more shields 902/210/414 are slidable in relation to the elongated hollow tubular member 904/604/404/204. According to some embodiments, the elongated hollow tubular member 904/604/404/204 comprises a slot 906 configured to fit at least a portion of the one or more shields 902/210/414. According to some embodiments, the slot 906 extends along a circumference of the elongated hollow tubular member 904/604/404/204 and is positioned within the wall of the elongated hollow tubular member 904/604/404/204.

According to some embodiments, the one or more shields 902/210/414 are slidable within the slot 906 in a plurality of directions, such as, for example, in a direction parallel to the longitudinal axis of the elongated hollow tubular member 904/604/404/204 and/or in a direction perpendicular to the longitudinal axis of the elongated hollow tubular member 904/604/404/204. According to some embodiments, at least a portion of the one or more shields 902/210/414 is rigid, semi-rigid, and/or flexible. According to some embodiments, the at least a portion of the one or more shields 902/210/414 is foldable within the slot 906.

According to some embodiments, the one or more shields are 902/210/414 are slidable within the slot 906 such that the one or more shields are rotatable in relation to a focal point of the curvature of the one or more shields and/or the longitudinal axis of the elongated hollow tubular member 904/604/404/204. According to some embodiments, the surgical instrument 600/400/200/104 comprises one or more rotational mechanisms configured to rotate the one or more shields in relation to the longitudinal axis of the elongated hollow tubular member 904/604/404/204, thereby allowing coverage of different portions of the end effector and/or the cutting head.

Reference is made to FIG. 10A, which is a cross sectional view schematic illustration of an exemplary rotation and extension mechanism of a shield, in accordance with some embodiments of the present invention.

According to some embodiments, the elongated hollow tubular member 1004/904/604/404/204 of the surgical instrument 1000/900/600/400/200/104 comprises a track 1006 positioned along an inner wall of the elongated hollow tubular member 1004/904/604/404/204. According to some embodiments, the track 1006 comprises an indentation configured to receive a portion of the one or more shields 1002/902/210/414. According to some embodiments, the one or more shields 1002/902/210/414 comprise one or more protuberances 1012 configured to fit within the track 1006. According to some embodiments, the one or more protuberances 1012 are configured to slide within the track 1006.

According to some embodiments, the track 1006 comprises longitudinal indentations 1010 and/or latitudinal indentations 1008. According to some embodiments, the track 1006 comprises a plurality of indentations forming angles ranging between 0-180 degrees with the longitudinal indentations 1010.

Figures 10B, 10C:
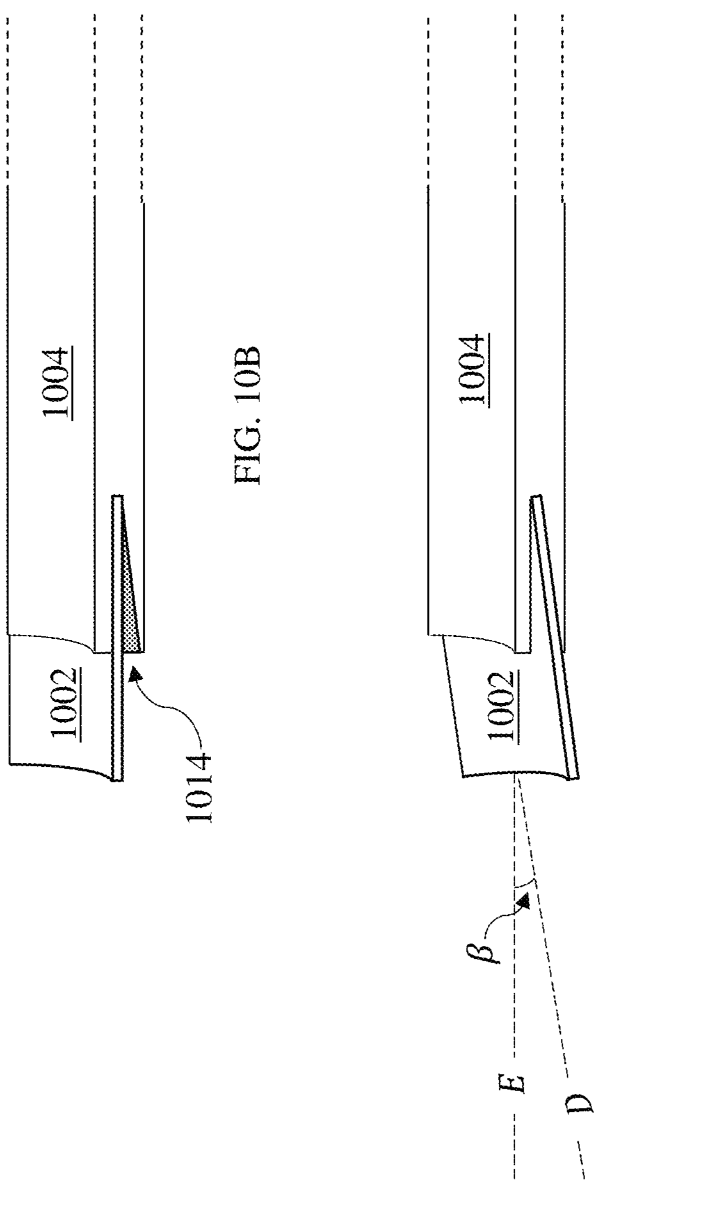
FIG. 10B and FIG. 10C are cross sectional view schematic illustrations of an exemplary tilting mechanism of a shield at a straight position and an angled position in relation to the elongated hollow tubular member, respectively, in accordance with some embodiments of the present invention.
Figures 10D, 10E:
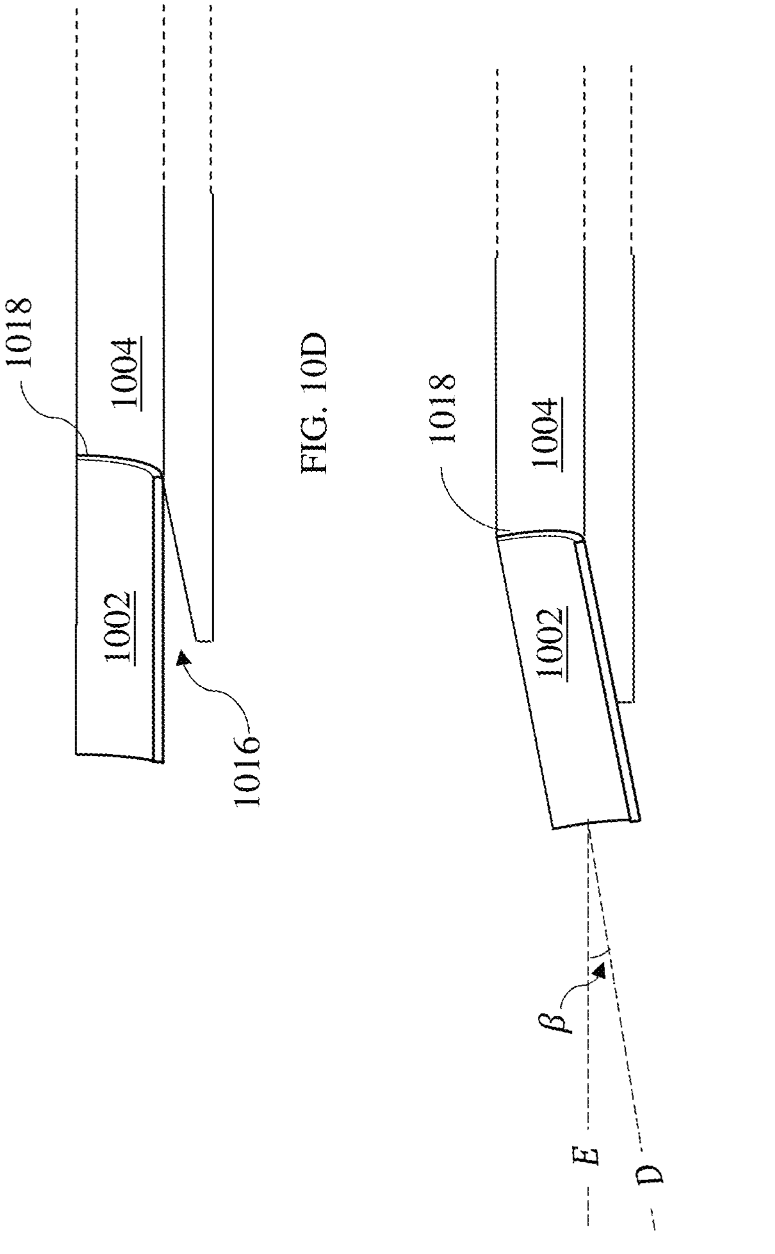
FIG. 10D and FIG. 10E are cross sectional view schematic illustrations of an exemplary tilting mechanism of a shield at a straight position and an angled position in relation to the elongated hollow tubular member, respectively, in accordance with some embodiments of the present invention.

Reference is made to FIG. 10B and FIG. 10C, which are cross sectional view schematic illustrations of an exemplary tilting mechanism of a shield at a straight position and an angled position in relation to the elongated hollow tubular member, respectively, in accordance with some embodiments of the present invention, and to FIG. 10D and FIG. 10E, which are cross sectional view schematic illustrations of an exemplary tilting mechanism of a shield at a straight position and an angled position in relation to the elongated hollow tubular member, respectively, in accordance with some embodiments of the present invention.

According to some embodiments, the one or more shields 1002/902/210/414 are moveably coupled to the surgical instrument and/or the elongated hollow tubular member 1004/904/604/404/204.

According to some embodiments, such as depicted in FIG. 10B and FIG. 10C, the one or more shields 1002/902/210/414 are positioned within a wall of the elongated hollow tubular member 1004/904/604/404/204. According to some embodiments, the wall of the elongated hollow tubular member 1004/904/604/404/204 comprises a slot 1014 configured to fit a portion of the one or more shields 1002/902/210/414. According to some embodiments, the slot 1014 is sized such that the angle (β) of the shield 1002/902/210/414 in relation to the elongated hollow tubular member 1004/904/604/404/204 is adjustable. According to some embodiments, the slot 1014 is sized such that the angle of the shield 1002/902/210/414 in relation to the end effector 812/800/700/608/412/208 is adjustable.

According to some embodiments, such as depicted in FIG. 10D and FIG. 10E, the one or more shields 1002/902/210/414 are coupled to a wall of the elongated hollow tubular member 1004/904/604/404/204 via a hinge 1018. According to some embodiments, at a straight position of the shield 1002/902/210/414 in relation to the elongated hollow tubular member 1004/904/604/404/204, such as depicted in FIG. 10D, the elongated hollow tubular member 1004/904/604/404/204 and the shield 1002/902/210/414 form a cavity 1016 therebetween. According to some embodiments, at least one of the shield 1002/902/210/414 and the elongated hollow tubular member 1004/904/604/404/204 comprises a tapered end.

According to some embodiments, the angle (β) of the shield 1002/902/210/414 in relation to the elongated hollow tubular member 1004/904/604/404/204 is defined as the angle between the longitudinal axis (E) of the elongated hollow tubular member 1004/904/604/404/204 and the longitudinal axis (D) of the shield 1002/902/210/414.

According to some embodiments, the processor is configured to command a change in the angle (β) and/or the angle between the shield 1002/902/210/414 and the end effector 812/800/700/608/412/208. According to some embodiments, the processor is configured to command the driving unit to drive the rotation of the shield about the longitudinal axis (E) of the elongated hollow tubular member 1004/904/604/404/204 and/or about the hinge 1018. According to some embodiments, the angle (β) and/or the angle between the shield 1002/902/210/414 and the end effector 812/800/700/608/412/208 can range between 0 to 80 degrees in a counterclockwise and/or clockwise direction. According to some embodiments, the shield 1002/902/210/414 is rotatable away from and/or towards the end effector 812/800/700/608/412/208.

Figure 11B:
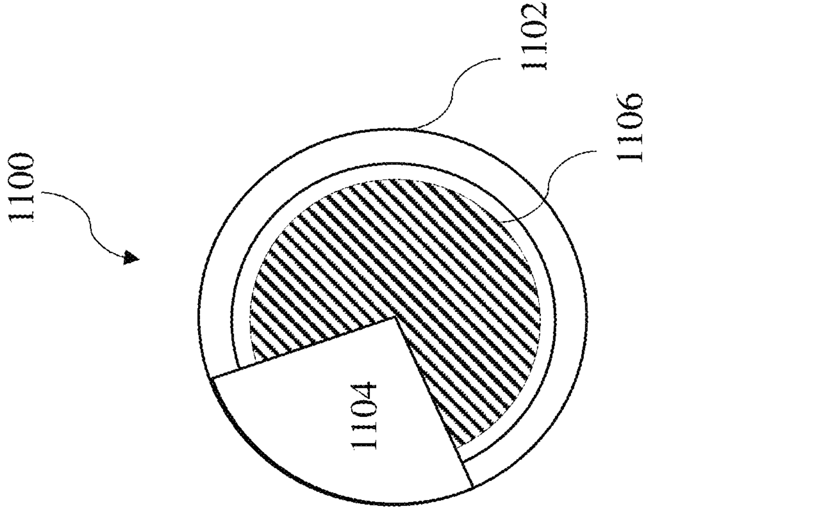
FIG. 11A and FIG. 11B are bottom view schematic illustrations of an exemplary elongation mechanism of a shield, in accordance with some embodiments of the present invention.
Figure 11A:
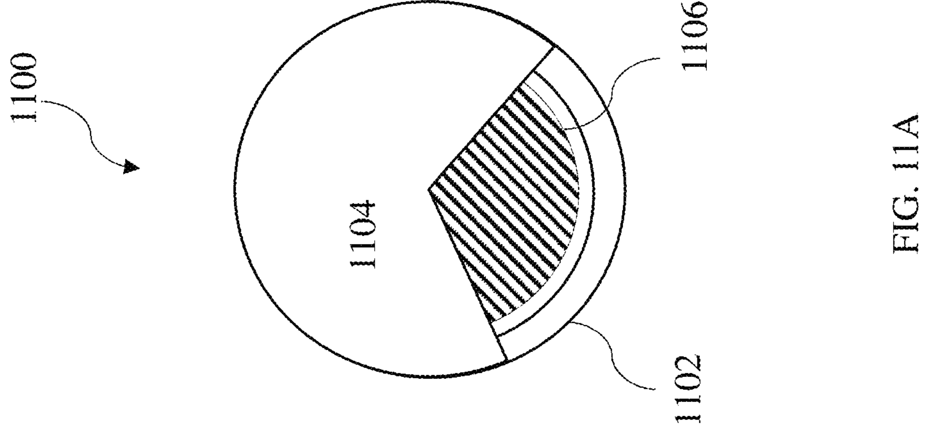

Reference is made to FIG. 11A and FIG. 11B, which are bottom view schematic illustrations of an exemplary elongation mechanism of a shield, in accordance with some embodiments of the present invention.

According to some embodiments, the angle of the shield 1102/1104/1002/902/210/414 is adjustable in relation to the end effector 1106/800/700/608/412/208. According to some embodiments, the shield 1102/1104/1002/902/210/414 comprises an elongation mechanism configured to elongate in a direction towards the longitudinal axis of the end effector 1106/800/700/608/412/208 and/or the elongated hollow tubular member 904/604/404/204. According to some embodiments, the shield 1102/1104/1002/902/210/414 comprises an elongation mechanism configured to elongate in a direction away from the longitudinal axis of the end effector 1106/800/700/608/412/208 and/or the elongated hollow tubular member 904/604/404/204.

According to some embodiments, the shield 1102/1104/1002/902/210/414 is configured to cover at least a portion of the bottom of the end effector 1106/800/700/608/412/208, such as depicted in FIG. 11A and FIG. 11B.

According to some embodiments, the shield 1102/1104/1002/902/210/414 as depicted in FIG. 11A and FIG. 11B is configured to rotate while cover at least a portion of the bottom of the end effector 1106/800/700/608/412/208. In some embodiments, the shield 1102/1104/1002/902/210/414 is configured to rotate and/or tilt in relation to the longitudinal axis (E) of the elongated hollow tubular member 1004/904/604/404/204, while the shield covers at least a portion of the bottom of the end effector 1106/800/700/700/608/412/208 as depicted in FIG. 9A, FIG. 9B, FIG. 10A, FIG. 10B, FIG. 10C, FIG. 10D, and FIG. 10E, and as described in greater detail elsewhere herein.

According to some embodiments, the processor is configured to command a change in any one or more of the elongation mechanisms, the rotation mechanisms, the extension, elongation, and rotation of the shield 1102/1104/1002/902/210/414 in relation to the end effector 1106/800/700/608/412/208 and/or the elongated hollow tubular member 904/604/404/204. According to some embodiments, the processor is configured to command the driving unit to drive the elongation, contraction, rotation, angle in relation to the end effector 1106/800/700/608/412/208, and/or extension of the shield 1102/1104/1002/902/210/414.

According to some embodiments, the shield 1102/1104/1002/902/210/414 is configured to separate between the end effector 1106/800/700/608/412/208 and tissue, thereby mitigating the risk of impacting the tissue by rotation of the end effector 1106/800/700/608/412/208. According to some embodiments, the shield 1102/1104/1002/902/210/414 is configured to mechanically separate between two tissue layers to facilitate introduction of the end effector 1106/800/700/608/412/208 to the target tissue. According to some embodiments, the shield 1102/1104/1002/902/210/414 is configured to rotate about a longitudinal axis thereof and/or tilt in relation to the end effector 1106/800/700/608/412/208, thereby mechanically separating between two tissue layers to facilitate introduction of the end effector 1106/800/700/608/412/208 to the target tissue.

Irrigation and Suction

According to some embodiments, the surgical instrument 1000/900/600/400/200/104 and/or the system 100 comprises an irrigation channel. According to some embodiments, the irrigation channel extends between the end effector 1106/800/700/700/608/412/208 and the handle of the surgical instrument 1000/900/600/400/200/104. According to some embodiments, the irrigation channel is coupled to a pump configured to pump fluid towards the end effector. Advantageously, pumping fluid towards the end effector 1106/800/700/700/608/412/208 enables cooling of the surgical instrument 1000/900/600/400/200/104 and/or portions of the surgical instrument 1000/900/600/400/200/104 during implementation and/or rotation of the end effector 1106/800/700/700/608/412/208. According to some embodiments, for an end effector that is and/or includes a cutting head, cooling of the end effector prevents heating of the cutting head during implementation and/or rotation thereof.

According to some embodiments, the surgical instrument surgical instrument 1000/900/600/400/200/104 and/or the system 100 comprises a suction channel configured for suction of debris and/or suction of the pumped fluid of the irrigation channel. According to some embodiments, the suction channel extends along a length of the elongated hollow tubular member 904/604/404/204. According to some embodiments, the suction channel extends into the handle 202/602. According to some embodiments, the suction channel is couplable with a suction unit.

According to some embodiments, the suction channel is positioned within a wall of the elongated hollow tubular member 904/604/404/204. According to some embodiments, the suction channel is positioned between the elongated hollow tubular member 904/604/404/204 and the end effector 1106/800/700/608/412/208.

According to some embodiments, the processor and/or driving unit is coupled to the suction unit and/or the pump of the irrigation channel. According to some embodiments, the processor and/or the driving unit are configured to control the operation of the suction unit.

Sensors and Camera

According to some embodiments, surgical instrument surgical instrument 1000/900/600/400/200/104 and/or the system 100 comprise one or more sensors. According to some embodiments, the one or more sensors are positioned along the elongated hollow tubular member 904/604/404/204.

According to some embodiments, the one or more sensors comprise a force sensor. According to some embodiments, the one or more sensors comprise one or more of pressure sensor, force sensor, temperature sensor, speedometer, accelerometer, proximity sensor, and infra-red sensor, or any combination thereof.

According to some embodiments, the sensor is configured to detect nerves. According to some embodiments, the senor comprises a nerve detecting device, such as, for example, Intraoperative Neuromonitoring (IONM). According to some embodiments, the surgical instrument 1000/900/600/400/200/104 and/or the system 100 comprise an electrophysiological monitoring device and/or neuro-stimulation device.

According to some embodiments, the surgical instrument surgical instrument 1000/900/600/400/200/104 comprises one or more electrodes, being thereby configured for electrophysiological monitoring and/or neurostimulation. According to some embodiments, the one or more electrodes are configured to function as a single electrode. The surgical instrument 1000/900/600/400/200/104 is thereby configured to allow establishing a voltage between the one or more electrodes and an external electrode placed on/in a body of a subject during a procedure and/or while the surgical instrument 1000/900/600/400/200/104 is in use. According to some alternative embodiments, the one or more electrodes include at least two electrodes configured to function as two electrodes of opposite polarity.

According to some embodiments, at least a portion of the surgical instrument 1000/900/600/400/200/104 is made of an electrically conducting material. According to some embodiments, the one or more sensor is configured to detect change in voltage of the one or more electrodes. According to some embodiments, the one or more sensor is in communication with the processor. According to some embodiments, the one or more sensor is configured to provide feedback regarding operation of the surgical instrument 1000/900/600/400/200/104. According to some embodiments, the processor is configured to receive data from the one or more sensors.

According to some embodiments, the processor is configured to adjust a position and/or special orientation of the robot arm 102 and or of the surgical instrument 1000/900/600/400/200/104 based on the data received from the one or more sensors. According to some embodiments, the processor is configured to adjust a length and/or position of one or more portion of the surgical instrument 1000/900/600/400/200/104 based on the data received from the one or more sensors.

According to some embodiments, the sensor comprises an image capturing device. According to some embodiments, the surgical instrument 1000/900/600/400/200/104 and/or the system 100 comprise one or more cameras. According to some embodiments, a distal end of the elongated hollow tubular member 904/604/404/204 comprises the one or more cameras configured for imaging of and area surrounding the end effector 1106/800/700/608/412/208. According to some embodiments, the one or more cameras are in communication with the processor. According to some embodiments, the processor is configured to receive images from the one or more cameras.

According to some embodiments, the processor is configured to adjust a position and/or special orientation of the robot arm 102 and or of the surgical instrument 1000/900/600/400/200/104 based on the images received from the one or more cameras. According to some embodiments, the processor is configured to adjust a length and/or position of one or more portion of the surgical instrument 1000/900/600/400/200/104 based on the images received from the one or more cameras.

Method

Figure 12A:
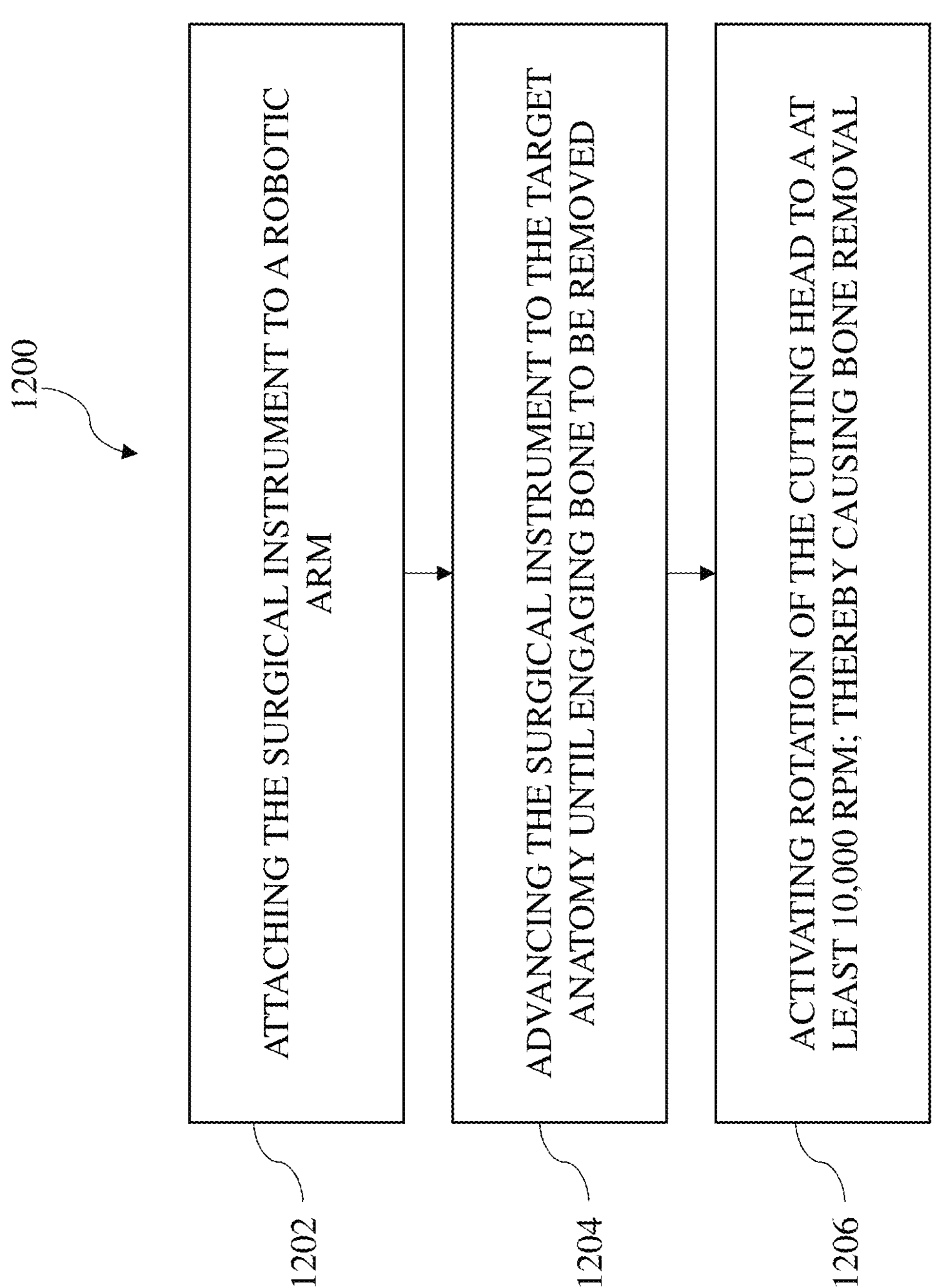
FIGS. 12A-12B is a flowchart of functional steps in a method for performing a robotic spinal decompression surgery, in accordance with some embodiments of the present invention.
Figure 12B:
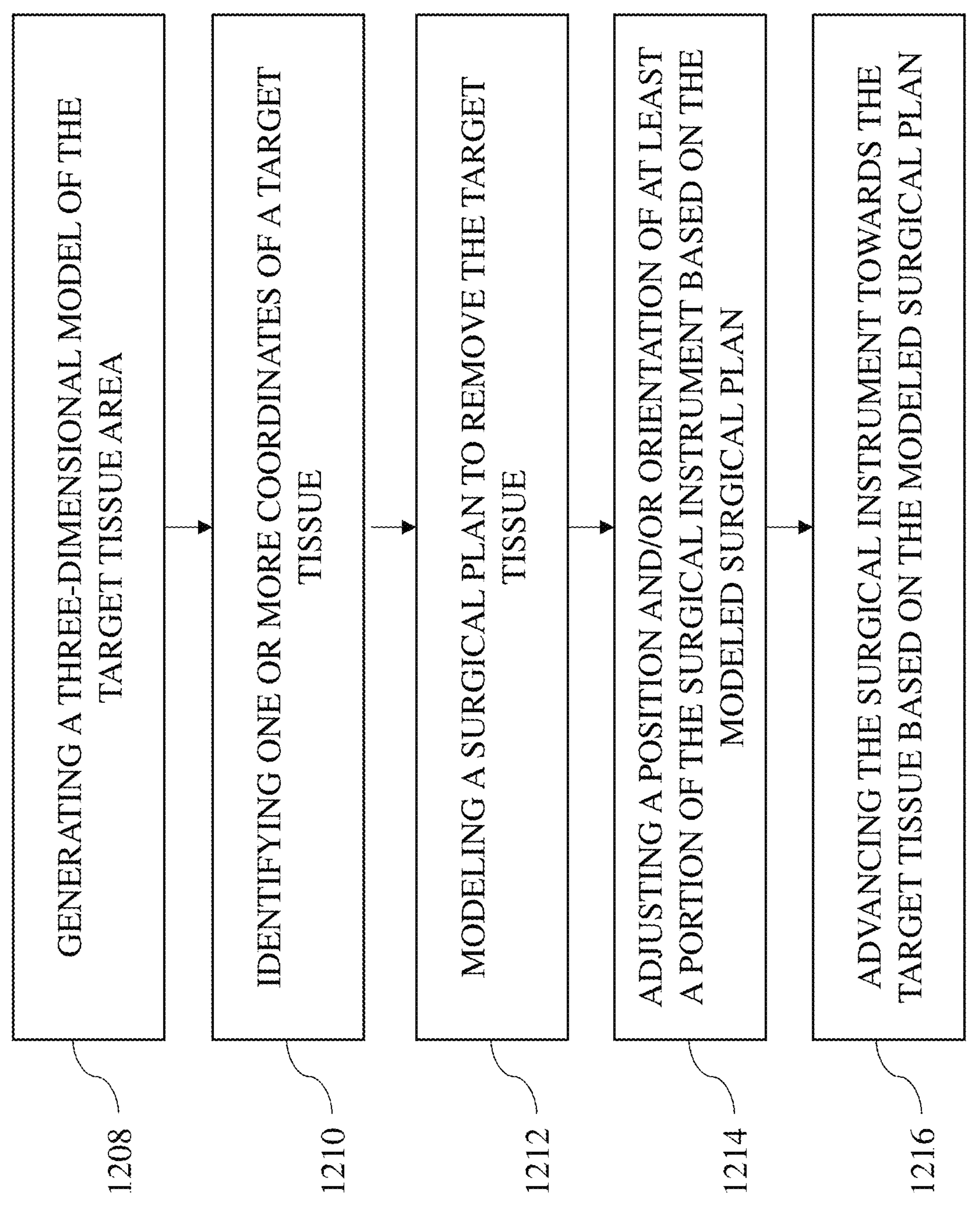

Reference is made to FIG. 12, which is a flowchart of functional steps in a method for performing a robotic spinal decompression surgery, in accordance with some embodiments of the present invention.

According to some embodiments, at step 1202, the method comprises attaching the surgical instrument to a robotic arm. According to some embodiments, the method comprises identifying a location of the target anatomy based on preoperative imaging. According to some embodiments, the method comprises determining an initial orientation of the elongated hollow tubular member based on the preoperative imaging. According to some embodiments, the method comprises determining an initial angle of the bend based on the preoperative imaging.

According to some embodiments, the method further comprises determining an initial degree of elongation of one or more of the one or more shields, the end effector, the elongated hollow tubular member, the proximal torque transfer element and the distal torque transfer element based on preoperative imaging. According to some embodiments, the method further comprises determining an initial degree of contraction of one or more of the one or more shields, the end effector, the elongated hollow tubular member, the proximal torque transfer element and the distal torque transfer element based on preoperative imaging.

According to some embodiments, the method comprises creating a surgical corridor to the target anatomy based on the preoperative imaging. According to some embodiments, at step 1204, the method comprises advancing the surgical instrument to the target anatomy until engaging bone to be removed. According to some embodiments, the method comprises exposing the neural element to be decompressed. According to some embodiments, the method comprises exposing the neural element to be decompressed prior to the activating the surgical instrument.

According to some embodiments, at step 1206, the method comprises activating rotation of the end effector to a at least 10,000 rpm; thereby causing bone removal. According to some embodiments, the method further comprises adjusting an orientation of the elongated hollow tubular member based on images obtained from the one or more cameras during surgery and/or based on data obtained from the one or more sensors during surgery. According to some embodiments, the method further comprises adjusting the angle of the bend based on images obtained from the one or more cameras during surgery and/or based on data obtained from the one or more sensors during surgery.

Figures 13, 14:
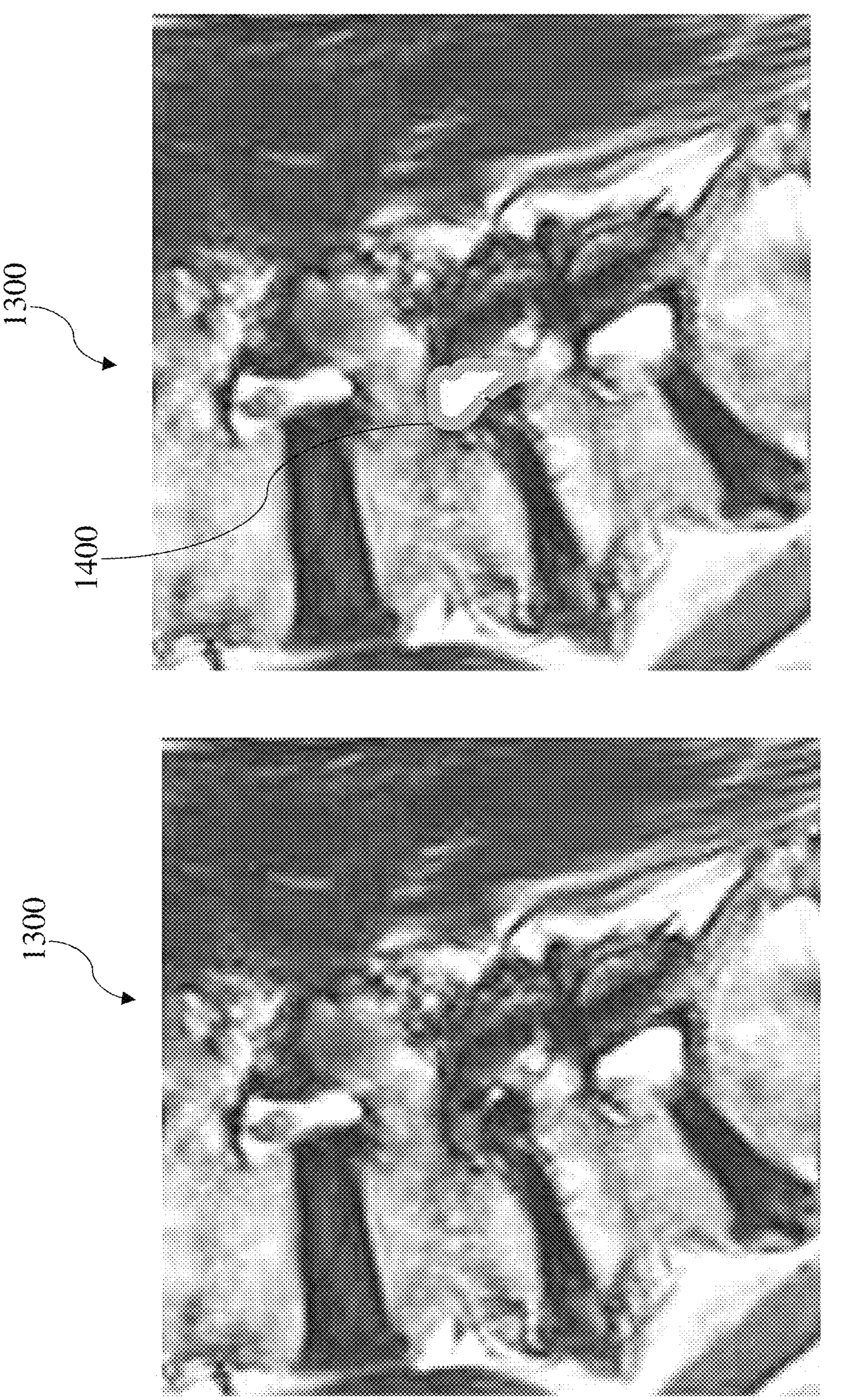
FIG. 13 is an exemplary preoperative scan, in accordance with some embodiments of the present invention.
FIG. 14 is an exemplary preoperative scan comprising coordinates of a target tissue, in accordance with some embodiments of the present invention.

Reference is made to FIG. 13, which is an exemplary preoperative scan, in accordance with some embodiments of the present invention.

According to some embodiments, the method further comprises adjusting an orientation, length, and/or position of the surgical instrument and/or a portion of the surgical instrument, based on data obtained from a scan of the subject during surgery and/or prior to the surgery, for example, such as a preoperative scan 1300 as depicted in FIG. 13. According to some embodiments, the scan comprises at least one of a CT scan, MRI, microscope, and/or endoscope imaging, or fusion of any combination thereof. According to some embodiments, the scan comprises data obtained from the one or more camera and/or sensors of the surgical instrument.

Figure 15:
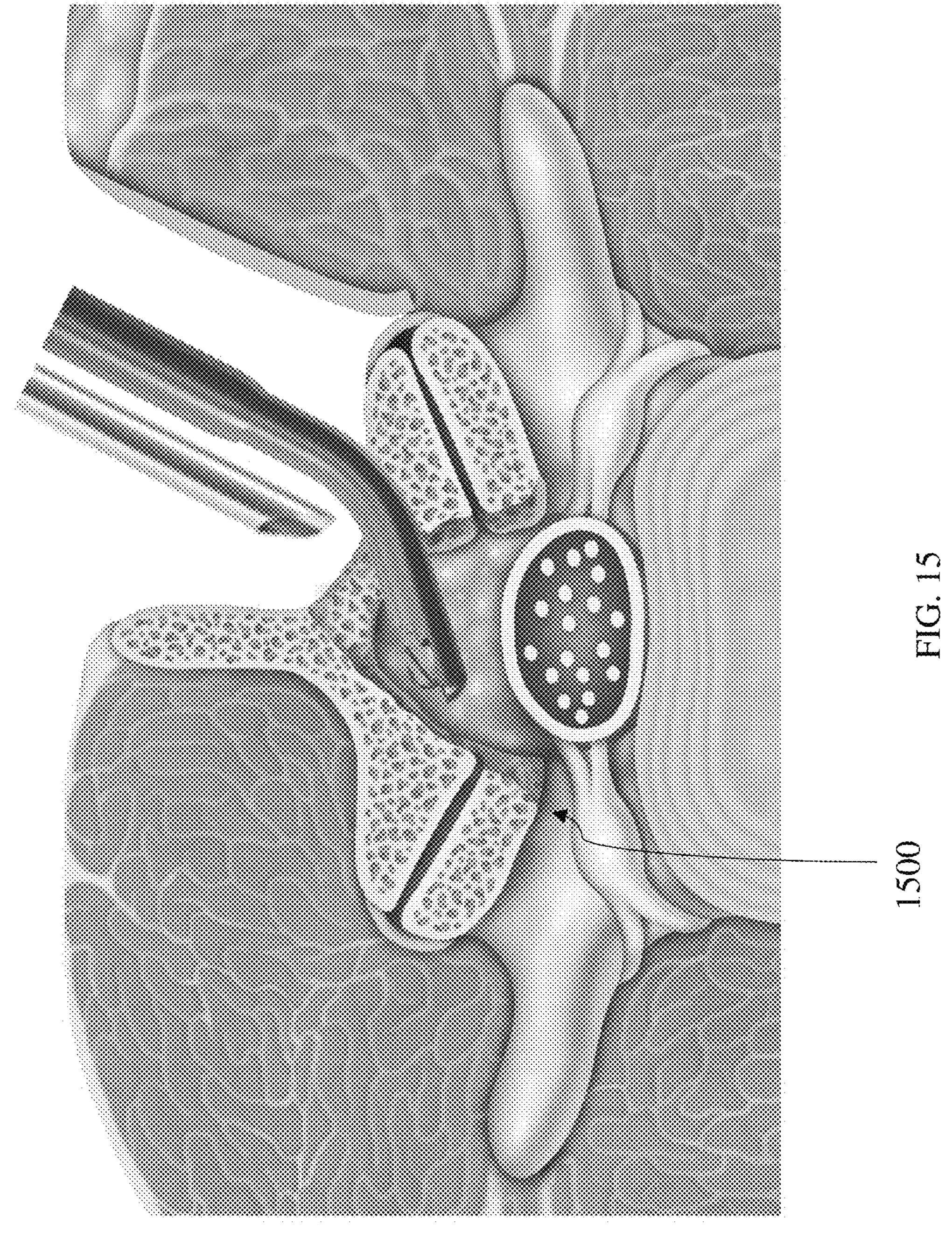
FIG. 15 is a side view schematic illustration of an exemplary implementation of the surgical instrument, in accordance with some embodiments of the present invention.
Figure 16:
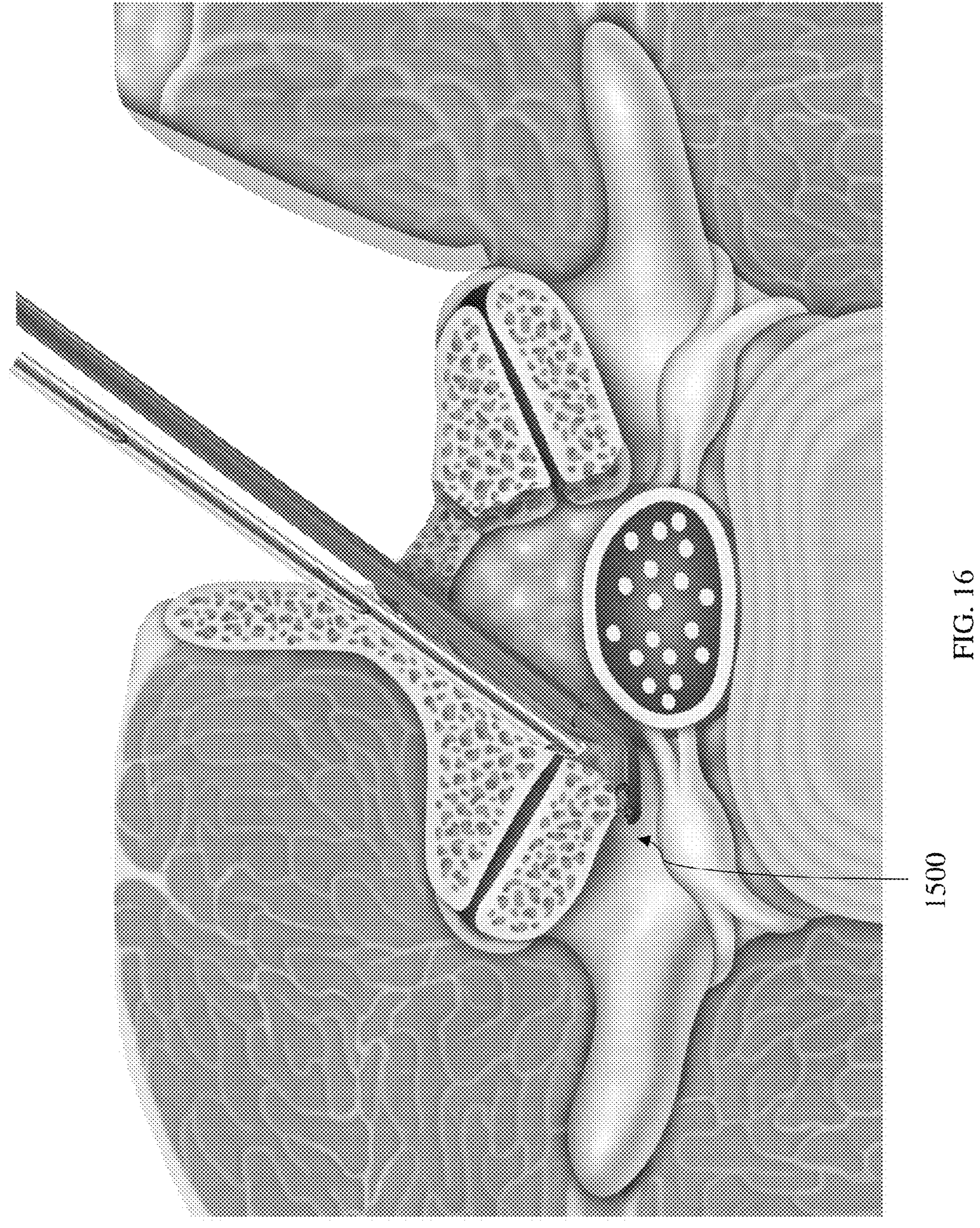
FIG. 16 is a side view schematic illustration of an exemplary implementation of the surgical instrument, in accordance with some embodiments of the present invention.

Reference is made to FIG. 14, which is an exemplary preoperative scan comprising coordinates of a target tissue, in accordance with some embodiments of the present invention, to FIG. 15, which is a side view schematic illustration of an exemplary implementation of the surgical instrument, in accordance with some embodiments of the present invention, and to FIG. 16, which is a side view schematic illustration of an exemplary implementation of the surgical instrument, in accordance with some embodiments of the present invention.

According to some embodiments, the method comprises identifying one or more coordinates of at least one target tissue area based on, at least in part, the obtained data and/or the scan of the subject, for example, the coordinates of the target tissue 1400 identified from the preoperative image 1300, such as depicted in FIG. 14. According to some embodiments, the target tissue is identified as tissue which should to be surgically removed. According to some embodiments, the method comprises positioning the surgical instrument at a position in which the target tissue can be removed by the surgical instrument, based, at least in part, on the identified coordinates of the target tissue. According to some embodiments, the method comprises adjusting a length of one or more portion of the surgical instrument based, at least in part, on the identified coordinates. According to some embodiments, the method comprises adjusting an orientation of one or more portion of the surgical instrument based, at least in part, on the identified coordinates. For example, in some embodiments, the method comprises extending the end effector of the surgical instrument in relation to the elongated hollow tubular member. According to some embodiments, the method comprises advancing the surgical instrument and/or end effector of the surgical instrument towards the target tissue 1500/1400, such as depicted in FIG. 15 and FIG. 16, According to some embodiments, the method comprises obtaining the scan of the subject in real time, or in other words, during the surgery and/or during operation of the surgical instrument. According to some embodiments, the method comprises identifying one or more coordinates of at least one target tissue in real time. According to some embodiments, the method comprises advancing the surgical instrument towards the target tissue in real time. According to some embodiments, the method comprises positioning the surgical instrument at a position in which the target tissue can be removed by the surgical instrument in real time.

A potential advantage of the method comprising identifying one or more coordinates of at least one target tissue in real time and/or positioning the surgical instrument at a position in which the target tissue can be removed by the surgical instrument in real time is in that the surgical instrument does not require a user to navigate the surgical instrument to the target tissue. According to some embodiments, the surgical instrument is fully automated. According to some embodiments, the processor is configured to receive the data from the one or more scans of the subject. According to some embodiments, the processor is configured to identify one or more coordinates of at least one target tissue. According to some embodiments, the processor is configured to identify one or more coordinates of at least one target tissue, based, at least in part, on the received data. According to some embodiments, the processor is configured to command a position, orientation, length, and/or relation between one or more portions of the surgical instrument.

According to some embodiments, the method comprises identifying one or more coordinates of one or more nerves of the subject in real time. According to some embodiments, the method comprises stopping or suspending a movement of the surgical instrument towards the target tissue in real time, based, at least in part, on data received from the sensor of the surgical instrument and/or data associated with at least one of the electrophysiological monitoring device, the neuro-stimulation device, and the one or more electrodes. According to some embodiments, the method comprises positioning the surgical instrument at a position in which the target tissue can be removed without damaging any nerves of the subject in real time, based, at least in part on data received from the sensor of the surgical instrument and/or data associated with at least one of the electrophysiological monitoring device, the neuro-stimulation device, and the one or more electrodes. According to some embodiments, the method further comprises adjusting the elongation, extension, and/or the relative angle of one or more of the one or more shields, the end effector and/or the cutting head, the elongated hollow tubular member, the proximal torque transfer element and the distal torque transfer element based on preoperative based on images obtained from the one or more cameras during surgery and/or based on data obtained from the one or more sensors during surgery.

Figures 17A, 17B:
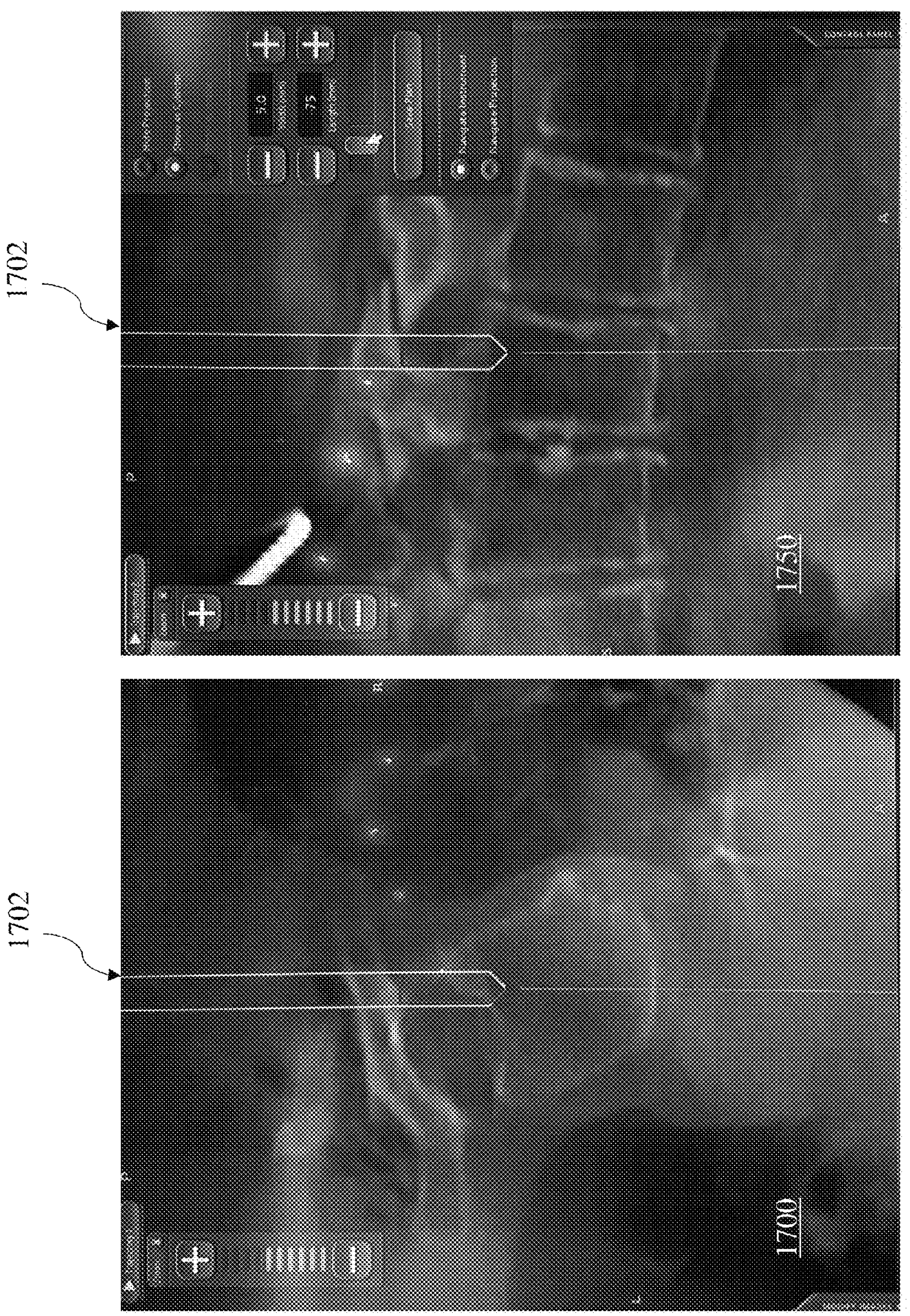
FIG. 17A and FIG. 17B are exemplary surgical plans, in accordance with some embodiments of the present invention.

Reference is made to FIG. 17A and FIG. 17B, which are exemplary surgical plans, in accordance with some embodiments of the present invention. According to some embodiments, identifying one or more coordinates comprises generating a model of the target tissue area. According to some embodiments, the target tissue comprises neural tissue which needs be decompressed. According to some embodiments, the model comprises two or three dimensions. For example, in some embodiments, such as depicted in FIG. 17A and FIG. 17B, each of the models 1700/1750 comprises two dimensions. According to some embodiments, the processor is configured to generate the model of the target tissue area. According to some embodiments, the model of the target tissue area is digital. According to some embodiments, the model of the target tissue area can be presented onto a display in communication with the processor.

According to some embodiments, the method comprises generating a surgical plan to remove the target tissue based on the identified one or more coordinates. According to some embodiments, the method comprises generating a model of the surgical plan in relation to the model of the target tissue area. According to some embodiments, the surgical plan comprises designing which portion of the bone to carve. According to some embodiments, the surgical plan comprises calculating a volume and/or shape of the portion of the bone which is to be carved.

For example, as depicted in FIG. 17A and FIG. 17B, the method comprises outlining an outline 1702 a position of the end effector and/or surgical instrument in relation to the models 1700/1750. According to some embodiments, the method comprises generating the surgical plan as a function of time. According to some embodiments, the processor is configured to generate the model of the surgical plan in relation to the model of the target tissue area.

According to some embodiments, the method comprises adjusting the elongation, extension, and/or the relative angle of one or more of the one or more shields, the end effector, the elongated hollow tubular member, the proximal torque transfer element and the distal torque transfer element based on the generated surgical plan. According to some embodiments, the method comprises adjusting a position and/or orientation of at least a portion of the surgical instrument based prior to advancing of the surgical instrument towards the target tissue. According to some embodiments, the method comprises adjusting a position and/or orientation of at least a portion of the surgical instrument after advancing of the surgical instrument towards the target tissue. According to some embodiments, the method comprises changing a position and/or orientation of at least a portion of the surgical instrument during the surgery.

According to some embodiments, the method comprises monitoring a position and/or orientation of the surgical instrument during the surgery and/or in real time. According to some embodiments, the method comprises monitoring a position and/or orientation of the surgical instrument in relation to the target tissue in real time. According to some embodiments, the method comprises monitoring a position and/or orientation of the surgical instrument in relation to the target tissue using one or more markers. According to some embodiments, the method comprises positioning one or more markers on the body of the subject surrounding an incision of the procedure.

A potential advantage of generating a model of the target tissue in real time is in that the method and/or surgical instrument enable a user to visualize an ongoing procedure in areas which are out of the line of sight of the user. For example, according to some embodiments, a user of the surgical instrument is able to identify a position of the surgical instrument in relation to the target tissue using the generated model and/or the identified coordinates of the target tissue modeled onto the generated model.

Figure 18A:
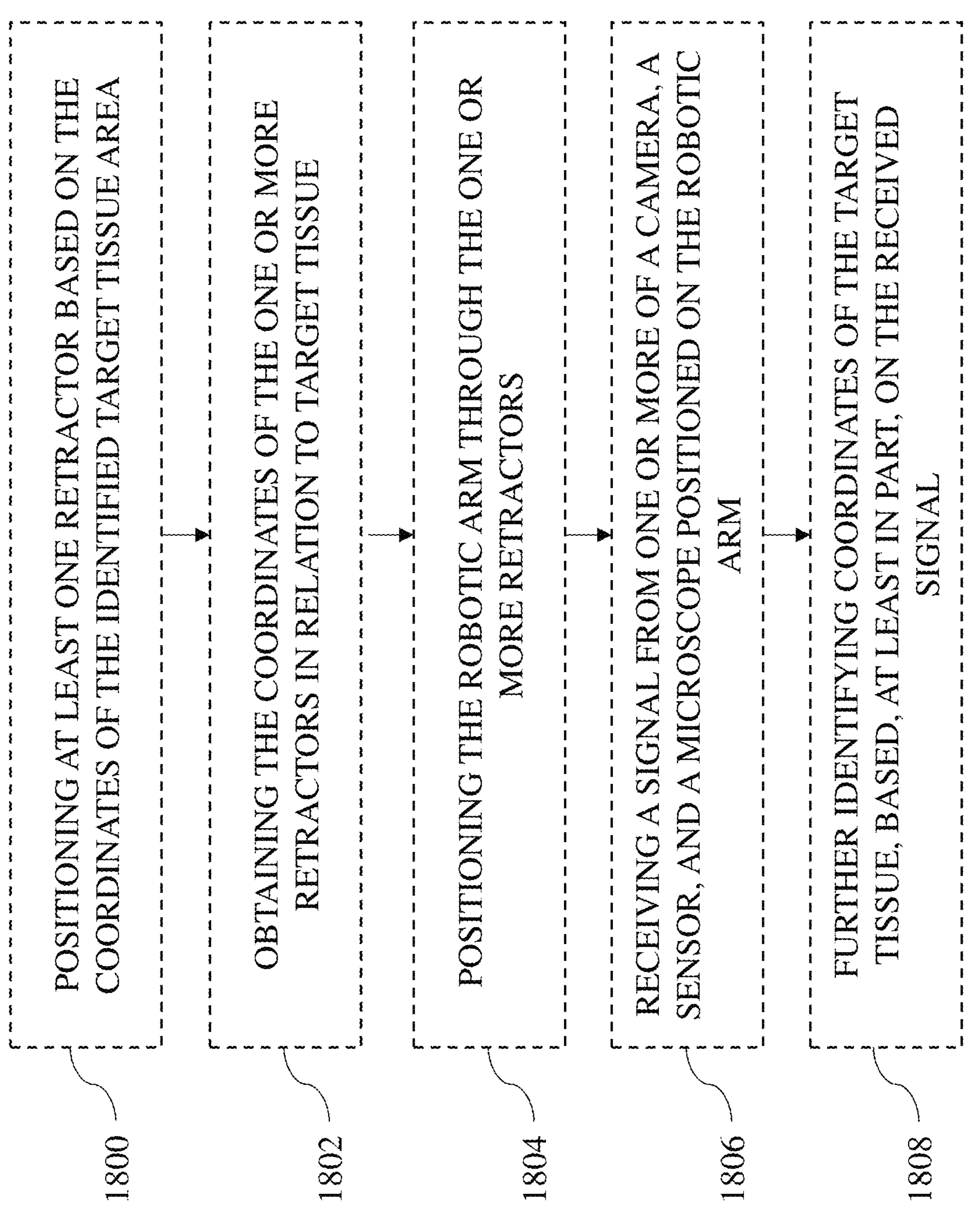
FIG. 18A and FIG. 18B are flowcharts of functional steps in an exemplary method for performing a robotic spinal decompression surgery, in accordance with some embodiments of the present invention.
Figure 18B:
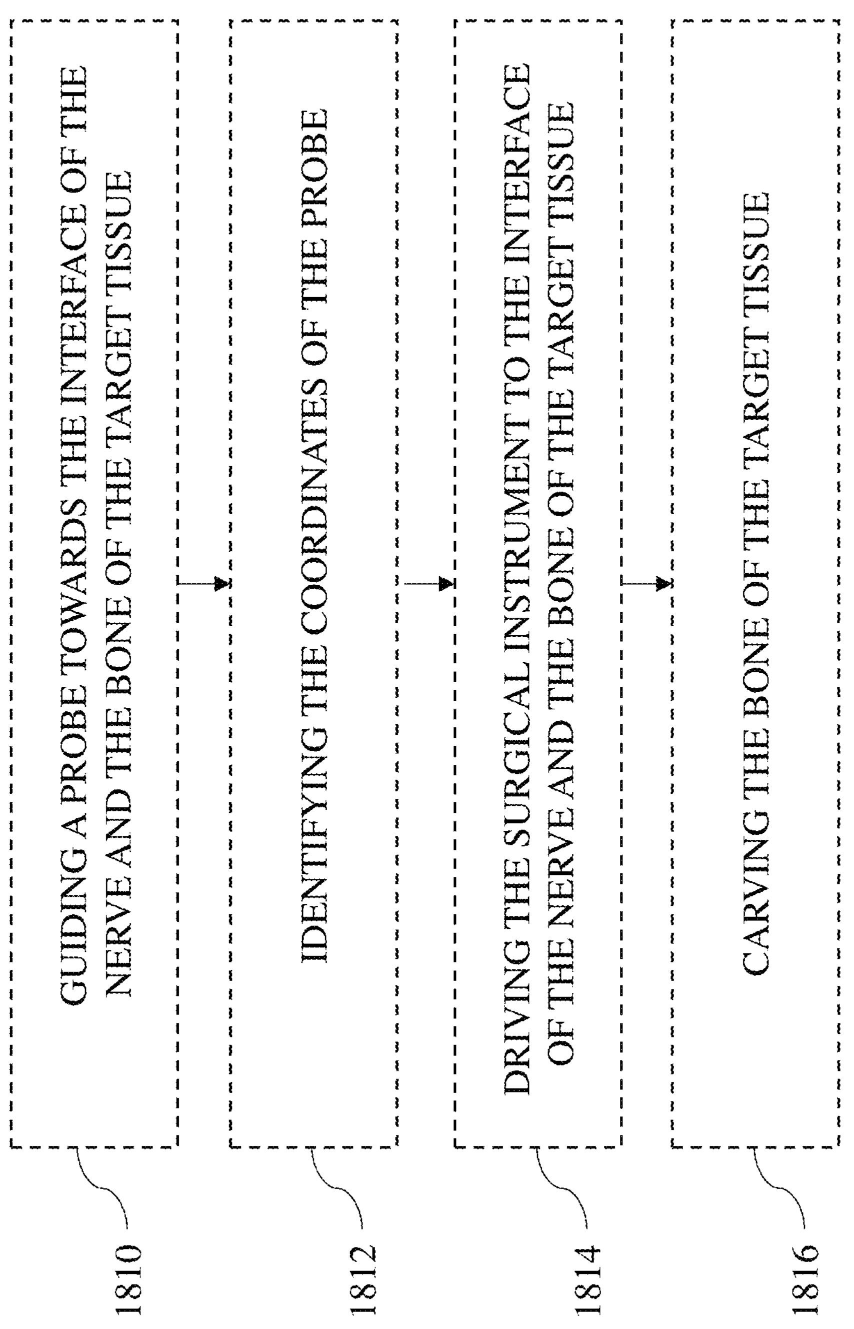

Reference is made to FIG. 18A and FIG. 18B, which are flowcharts of functional steps in an exemplary method for performing a robotic spinal decompression surgery, in accordance with some embodiments of the present invention. Optionally, and according to some embodiments, the steps of the method of FIG. 18A and FIG. 18B can be incorporated into the method 1200.

According to some embodiments, the method comprises acquiring the coordinates of the one or more markers using a stereotactic system. According to some embodiments, the method comprises incorporating the coordinates of the markers to model of the target tissue area. According to some embodiments, the method comprises obtaining data regarding the position of the one or more markers and the surgical area simultaneously using an intra-operative scan. According to some embodiments, the method comprises identifying the target tissue based, at least in part, on the intra-operative scan. According to some embodiments, the method comprises generating the surgical plan based, at least in part, on the intra-operative scan.

According to some embodiments, the surgical plan comprises the amount, shape, and/or volume of tissue to be removed during operation. According to some embodiments, the surgical plan comprises determining a rotation speed of the end effector during one or more portions of the operation. According to some embodiments, the surgical plan comprises an irrigation plan for one or more portions of the operation. According to some embodiments, the irrigation plan comprises at least one of a time of irrigation. According to some embodiments, the surgical plan comprises an operational plan for the suction channel and/or the pump.

According to some embodiments, at step 1800, the method comprises positioning one or more retractors based on the coordinates of the identified target tissue. According to some embodiments, the retractor comprises a tubular shape. According to some embodiments, the method comprises implementing one or more dilators or a series of dilators. According to some embodiments, the one or more retractors comprise one or more markers. According to some embodiments, the method comprises obtaining coordinates of the one or more retractors. According to some embodiments, the method comprises obtaining the coordinated of the one or more retractors using one or more of the one or more markers and the stereotactic system. According to some embodiments, at step 1802, the method comprises obtaining the coordinates of the one or more retractors in relation to the body of the subject and/or in relation to the location of the target tissue.

According to some embodiments, at step 1804, the method comprises positioning the robotic arm through the one or more retractors. According to some embodiments, the method comprises advancing the robotic arm through the retractor, based, at least in part, on the identified coordinates of at least one of the retractor and the target tissue area. According to some embodiments, the method comprises exposing the target tissue. According to some embodiments, the target tissue comprises neural tissue to be decompressed, and the method comprises exposing the target tissue by removing soft tissue.

According to some embodiments, at step 1806, the method comprises receiving a signal from one or more of a camera, a sensor, microscope, and/or endoscope positioned on the robotic arm. According to some embodiments, the method comprises receiving a signal from the one or more sensors. According to some embodiments, at step 1808, the method comprises identifying the target tissue, based, at least in part, on the received signal from one or more of a camera, sensor, microscope, and/or endoscope, positioned on the robotic arm. According to some embodiments, the method comprises identifying nerves using one or more of the received signals.

According to some embodiments, at step 1810, the method comprises guiding a probe towards the interface of the nerve and the bone of the target tissue. According to some embodiments, the method comprises positioning the probe at the interface of the bone and the nerve of the target tissue. According to some embodiments, at step 1812, the method comprises identifying coordinates of the probe in relation to at least one of the retractor, the body of the subject, and the target tissue. According to some embodiments, the method comprises identifying the coordinates of the probe using the stereotactic system.

According to some embodiments, the method comprises driving the surgical instrument using a robotic arm. According to some embodiments, the method comprises driving the surgical instrument towards the coordinates of the probe. According to some embodiments, the method comprises driving the surgical instrument through the one or more retractors. According to some embodiments, the method comprises driving the surgical instrument to the target tissue. According to some embodiments, at step 1814, the method comprises driving the surgical instrument to the interface of the nerve and the bone of the target tissue such that the shield is positioned between the end effector and the nerve of the target tissue.

According to some embodiments, the method comprises driving the surgical instrument to the interface of the nerve and the bone of the target tissue such that the end effector is positioned between the shield and the bone of the target tissue. According to some embodiments, at step 1816, the method comprises carving the bone of the target tissue. According to some embodiments, the method comprises carving the bone of the target tissue, in accordance with the surgical plan. According to some embodiments, the method comprises carving the bone of the target tissue automatically without user intervention, by operating the surgical instrument according to the surgical plan. According to some embodiments, the method comprises carving the bone of the target tissue manually using user input which operates one or more portions of the surgical instrument.

According to some embodiments, the method comprises verifying no damage was done to the nerve of the target tissue. According to some embodiments, the method comprises verifying by moving the probe thereby using tactile sensing of the nerve.

The following examples are presented in order to more fully illustrate some embodiments of the invention. They should in no way be construed, however, as limiting the broad scope of the invention. One skilled in the art can readily devise many variations and modifications of the principles disclosed herein without departing from the scope of the invention.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A robotic system for spinal decompression surgery comprising:

a. a robotic arm having multi-degree of freedom;

b. a surgical instrument configured to be received by the robotic arm; wherein the surgical instrument comprises:

a non-flexible elongated hollow tubular member comprising a bend at a distal end thereof and a bending mechanism, wherein an angle of the bend is structurally and intraoperatively adjustable via the bending mechanism; and a bendable flexible drive shaft positionable within the elongated hollow tubular member; and an end effector coupled to the flexible drive shaft, wherein the end effector comprises a cutting head, wherein the drive shaft is configured to transfer torque and rotational speed from a proximal end of the elongated hollow member, through the bend and to the end effector, and wherein the drive shaft is configured to transfer torque and rotational speed of at least 10,000 rpm, from a proximal end of the elongated member, to the end effector; and c. a processor configured to control the position of the robotic arm and/or the surgical instrument relative to a target tissue, and to control the bending mechanism to thereby enable intraoperatively changing the angle of the adjustable bend, while maintaining the position of the robotic arm and the surgical instrument;

d. a driving unit configured to control the operation of the surgical instrument based on inputs from the processor.

2. The system of claim 1, wherein the surgical instrument comprises a sensor positioned at the elongated shaft, the sensor configured to provide feedback to the processor regarding operation of the surgical instrument and to enable tracking a position of the surgical instrument in real time in relation to the target tissue.

3. The system of claim 1, wherein the end effector or one or more sections of the elongated hollow tubular member is elongatable along its longitudinal axis and wherein the elongation is controllable via the processor.

4. The system of claim 1, wherein the elongated hollow tubular member comprises a shield configured to cover a portion of the end effector and a tilting mechanism, and wherein the processor is configured to control the tilting mechanism thereby enabling changing an angle of the shield relative to the end effector intraoperatively.

5. The system of claim 1, wherein a distal end of the elongated hollow tubular member comprises one or more cameras microscope, and/or endoscope configured for imaging of and area surrounding the end effector and wherein the processor is configured to receive images from the one or more cameras microscope, and/or endoscope.

6. The system of claim 5, wherein the processor is configured to adjust positioning of the robotic arm and or of the surgical instrument based on the images received from the one or more cameras, microscopes, and/or endoscopes.

7. The system of claim 1, wherein the surgical instrument comprises a handle, wherein the elongated hollow tubular member is axially rotatable relative to the handle and wherein the processor is configured to control the orientation and/or position of at least a portion of the surgical instrument.

8. The system of claim 1, comprising at least one marker positioned at a fixed location in relation to the surgical instrument such that an orientation of the surgical instrument is trackable by tracking a location of the at least one marker in real time in relation to the target tissue.

9. A surgical instrument for robotic spinal decompression surgery, the surgical instrument comprising:

a handle;

an end effector;

a non-flexible elongated hollow tubular member extending from the handle, the elongated hollow tubular having a bend at a distal end thereof; and a flexible core positionable within the elongated hollow tubular member, the flexible drive shaft configured to transfer torque and rotational speed of at least 10,000 rpm, from a proximal end of the elongated member, through the bend and to the end effector;

one or more torque transfer element connected to the flexible drive shaft; and an elongation mechanism;

wherein the elongated hollow tubular member, the end effector and/or the torque transfer element are intraoperatively structurally elongatable via the elongation mechanism, thereby allowing advancement of the end effector, while maintaining the surgical instrument and a surgical arm grasping the surgical instrument in a fixed position, and wherein the elongation mechanism is configured to be controlled by a processor.

10. The surgical instrument of claim 9, further comprising a sensor positioned at the elongated shaft, the sensor configured to provide feedback regarding operation of the surgical instrument, and to enable tracking a position of the surgical instrument in real time in relation to the target tissue.

11. The surgical instrument of claim 9, further comprising a bending mechanism and wherein an angle of the bend is intraoperatively adjustable via the bending mechanism.

12. The surgical instrument of claim 9, wherein the elongated hollow tubular member comprises a shield configured to cover a portion of the end effector and a tilting mechanism, and wherein an angle of the shield relative to the end effector is e intraoperatively adjustable via the tilting mechanism.

13. The system of claim 9, wherein a distal end of the elongated hollow tubular member comprises one or more cameras configured for imaging of and area surrounding the end effector.

14. The method of claim 9, further comprising an elongation mechanism and wherein the method further comprises adjusting the elongation of one or more of the shield, the end effector, the elongated hollow tubular member, the proximal torque transfer element and the distal torque transfer element, via the elongation mechanism based on the feedback obtained from one or more of the sensor, the camera, the microscope, and/or the endoscope in real time.

15. The method of claim 9, further comprising determining an initial degree of elongation of one or more of the shield, end effector, the elongated hollow tubular member, the proximal torque transfer element and the distal torque transfer element based on preoperative imaging.

16. The method of claim 9, further comprising identifying one or more coordinates of at least one target tissue area based on a scan of the subject and/or based on obtained data from at least one of the sensor, the camera, microscope, and the endoscope coupled to the surgical instrument, in real time.

17. The method of claim 16, further comprising adjusting one or more of a length, orientation, and position of one or more portions of the surgical instrument based on the identified coordinates, such that the target tissue can be removed by the surgical instrument.

18. A method for performing a robotic spinal decompression surgery, the method comprises:

attaching a surgical device comprising a non-flexible elongated hollow tubular member comprising a bend at a distal end thereof and a bending mechanism, wherein an angle of the bend is structurally and intraoperatively adjustable via the bending mechanism, a flexible drive shaft positionable within the elongated hollow tubular member, and an end effector, wherein the drive shaft is configured to transfer torque and rotational speed from a proximal end of the elongated hollow member, through the bend and to the end effector, and wherein the drive shaft is configured to transfer torque and rotational speed of at least 10,000 rpm, from a proximal end of the elongated member to the end effector;

advancing the surgical instrument to the target anatomy until engaging bone to be removed; and activate rotation of the end effector to a at least 10,000 rpm; thereby causing bone removal, and intraoperatively triggering, via a processor, adjustment of an angle of the adjustable bend of the elongated hollow tubular member, based on feedback obtained in real time from one or more of a sensor, a camera, a microscope, and/or an endoscope configured to track a position of the surgical instrument in real time in relation to the target tissue, such that the position of the end effector is changed while the position of the robotic arm and the surgical instrument is maintained.

* * * * *